(12) United States Patent
Nieswandt et al.

(10) Patent No.: US 11,028,144 B2
(45) Date of Patent: Jun. 8, 2021

(54) SOLUBLE GLYCOPROTEIN V FOR TREATING THROMBOTIC DISEASES

(71) Applicant: JULIUS-MAXIMILIANS-UNIVERSITÄT WÜRZBURG, Würzburg (DE)

(72) Inventors: Bernhard Nieswandt, Eibelstadt (DE); Sarah Beck, Würzburg (DE); David Stegner, Würzburg (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 185 days.

(21) Appl. No.: 16/065,365

(22) PCT Filed: Dec. 23, 2016

(86) PCT No.: PCT/EP2016/082629
§ 371 (c)(1),
(2) Date: Jun. 22, 2018

(87) PCT Pub. No.: WO2017/109212
PCT Pub. Date: Jun. 29, 2017

(65) Prior Publication Data
US 2019/0169265 A1    Jun. 6, 2019

(30) Foreign Application Priority Data
Dec. 23, 2015 (EP) .................................. 15202530

(51) Int. Cl.
| | | |
|---|---|---|
| *A61K 38/36* | (2006.01) |
| *C07K 14/705* | (2006.01) |
| *A61K 38/17* | (2006.01) |
| *A61K 47/61* | (2017.01) |
| *A61K 47/60* | (2017.01) |
| *A61P 7/02* | (2006.01) |
| *A61P 9/10* | (2006.01) |
| *A61K 38/38* | (2006.01) |
| *A61K 38/40* | (2006.01) |
| *A61K 45/06* | (2006.01) |
| *C07K 14/76* | (2006.01) |
| *C07K 14/79* | (2006.01) |

(52) U.S. Cl.
CPC ...... *C07K 14/70596* (2013.01); *A61K 38/177* (2013.01); *A61K 38/38* (2013.01); *A61K 38/40* (2013.01); *A61K 45/06* (2013.01); *A61K 47/60* (2017.08); *A61K 47/61* (2017.08); *A61P 7/02* (2018.01); *A61P 9/10* (2018.01); *C07K 14/76* (2013.01); *C07K 14/79* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| 4,399,216 A | 8/1983 | Axel et al. |
| 6,005,089 A * | 12/1999 | Lanza .................. C07K 14/705 |
| | | 435/252.3 |
| 6,403,077 B1 | 6/2002 | Strom et al. |
| 7,256,253 B2 | 8/2007 | Bridon et al. |
| 2004/0087778 A1 | 5/2004 | Feige et al. |

FOREIGN PATENT DOCUMENTS

| EP | 0117058 A2 | 8/1984 |
| EP | 0117060 A2 | 8/1984 |
| WO | WO 199502054 A2 | 1/1995 |
| WO | WO 2003076567 A2 | 9/2003 |
| WO | WO 2004101740 A2 | 11/2004 |
| WO | WO 2005000892 A2 | 1/2005 |
| WO | WO 2005001025 A2 | 1/2005 |
| WO | WO 2005063808 A1 | 7/2005 |
| WO | WO 2006000448 A2 | 1/2006 |
| WO | WO 2007090584 A1 | 8/2007 |
| WO | WO 2013120939 A1 | 8/2013 |

OTHER PUBLICATIONS

Graham F. L. et al., "A New Technique for the Assay of Infectivity of Human Adenovirus 5 DNA", Virology, 1973, vol. 52, pp. 456-467.
Graham F. L. et al., "Characteristics of a Human Cell Line Transformed by DNA from Human Adenovirus Type 5", J. Gen. Virol., 1977, vol. 36, pp. 59-72.
Mantei N. et al., "Rabbit β-globin mRNA production in mouse L cells transformed with cloned rabbit β-globin chromosomal DNA", Nature, 1979, vol. 281, pp. 40-46.
Mather J. P., "Establishment and Characterization of Two Distinct Mouse Testicular Epithelial Cell Lines", Biology of Reproduction, 1980, vol. 23, pp. 243-252.
Urlaub G. et al., "Isolation of Chinese Hamster Cell Mutants Deficient in Dihydrofolate Reductase Activity", Proc. Natl. Acad. Sci., 1980, vol. 77, No. 7, pp. 4216-4220.
Gething M-J. et al., "Cell-surface Expression of influenza haemagglutinin from a cloned DNA copy of the RNA gene", Nature, 1981, vol. 293, pp. 620-625.
Mather J. P., "Culture of Testicular Cells in Hormone-Supplemented Serum-Free Medium", Annals New York Academy of Sciences, 1982, vol. 383, pp. 44-68.
White, II G. C. et al., "Glycoprotein V Hydrolysis by Thrombin. Lack of Correlation with Secretion", Thrombosis Research, 1985, vol. 38, pp. 641-648.
Mansour S. L. et al., "Disruption of the proto-oncogene int-2 in mouse embryo-derived stem cells: a general strategy for targeting mutations to non-selectable genes", Nature, 1988, vol. 336, pp. 348-352.
Keown W. A. et al, "Methods for Introducing DNA into Mammalian Cells", Methods of Enzymology, 1990, vol. 185, pp. 527-537.
(Continued)

*Primary Examiner* — Michael Szperka
(74) *Attorney, Agent, or Firm* — Finnegan, Henderson, Farabow, Garrett & Dunner, LLP

(57) ABSTRACT

A soluble polypeptide comprising a modified glycoprotein V (GPV) lacking a functional transmembrane domain for use in the treatment or prevention of a thrombotic disease in a subject, said treatment or prevention comprising administering to the subject an effective amount of said soluble polypeptide.

19 Claims, 3 Drawing Sheets

Specification includes a Sequence Listing.

(56) References Cited

OTHER PUBLICATIONS

Hawley-Nelson P. et al., "LipofectAMINE™ Reagent: A New, Higher Efficiency Polycationic Liposome Transfection Reagent", Focus, 1993, vol. 15, No. 3, pp. 73-79.

Lanza F. et al., "Cloning and Characterization of the Gene Encoding the Human Platelet Glycoprotein V", The Journal of Biology Chemistry, 1993, vol. 268, No. 28, pp. 20801-20807.

Ravanat C. et al., "Gene Cloning of Rat and Mouse Platelet Glycoprotein V: Identification of Megakaryocyte-Specific Promoters and Demonstration of Functional Thrombin Cleavage", Blood, 1997, vol. 89, No. 9, pp. 3253-3262.

Dong J-F. et al., "Synthesis Assembly, and Intercellular Transport of the Platelet Glycoprotein Ib-IX-V Complex", The Journal of Biological Chemistry, 1998, vol. 273, No. 47, pp. 31449-31454.

Kahn M. L. et al., "A Dual Thrombin Receptor System for Platelet Activation", Nature, 1998, vol. 394, pp. 690-694.

Azorsa D. O. et al., "Measurement of GPV Released by Activated Platelets Using a Sensitive Immunocapture ELISA—Its Use to Follow Platelet Storage in Transfusion", Thromb. Haemost., 1999, vol. 81, pp. 131-138.

Kahn M. L. et al., "Glycoprotein V-Deficient Platelets Have Undiminished Thrombin Responsiveness and Do Not Exhibit a Bernard-Soulier Phenotype", Blood, 1999, vol. 94, No. 12, pp. 4112-4121.

Ramakrishnan V. et al., "Increased Thrombin Responsiveness in Platelets from Mice Lacking Glycoprotein V", Proc. Natl. Acad. Sci., 1999, vol. 96, No. 23, pp. 13336-13341.

Tatusova T. A. et al., "BLAST 2 Sequences, a new tool for comparing protein and nucleotide sequences", FEMS Microbiology Letters, 1999, vol. 174, pp. 247-250.

Coughlin S. R., "Thrombin Signalling and Protease-Activated Receptors", Nature, 2000, vol. 407, pp. 258-264.

Cunningham M. A. et al., "Protease-Activated Receptor 1 Mediates Thrombin-Dependent, Cell-Mediated Renal Inflammation in Crescentic Glomerulonephritis", J. Exp. Med., 2000, vol. 191, No. 3, pp. 455-461.

Nakanishi-Matsui M. et al., "PAR3 is a Cofactor for PAR4 Activation by Thrombin", Nature, 2000, vol. 404, pp. 609-613.

Shapiro M. J. et al., "Protease-activated Receptors 1 and 4 are Shut off with Distinct Kinetics after Activation by Thrombin", The Journal of Biological Chemistry, 2000, vol. 275, No. 33, pp. 25216-25221.

Garton K. J. et al., "Tumor Necrosis Factor-α-converting Enzyme (ADAM17) Mediates the Cleavage and Shedding of Fractalkine (CX3CL1)", The Journal of Biological Chemistry, 2001, vol. 276, No. 41, pp. 37993-38001.

Ni H. et al., "Increased thrombogenesis and embolus formation in mice lacking glycoprotein V", Blood, 2001, vol. 98, No. 2, pp. 368-373.

Nieswandt B. et al., "Platelet-Collagen Interaction: Is GPVI the Central Receptor?", Blood, 2003, vol. 102, No. 2, pp. 449-461.

Bergmeier W. et al., "GPVI down-regulation in murine platelets through metalloproteinase-dependent shedding", Thromb Haemost, 2004, vol. 91, pp. 951-958.

Canobbio I. et al., "Signalling Through the Platelet Glycoprotein Ib-V-IX Complex", Cellular Signalling, 2004, vol. 16, pp. 1329-1344.

Gardiner E. E. et al., "Regulation of platelet membrane levels of glycoprotein VI by a platelet-derived metalloproteinase", Blood, 2004, vol. 104, No. 12, pp. 3611-3617.

Di Nisio M. et al, "Direct Thrombin Inhibitors", The New England Journal of Medicine, 2005, vol. 353, No. 10, pp. 1028-1040.

Wolff V. et al., "Soluble Platelet Glycoprotein V Is a Marker of Thrombosis in Patients with Ischemic Stroke", Stroke, 2005, vol. 36, pp. e17-e19.

Dumont J. A. et al., "Monomeric Fc Fusions", Biodrugs, 2006, vol. 20, No. 3, pp. 151-160.

Eriksson B. I. et al., "A Once-Daily, Oral, Direct Factor Xa Inhibitor, Rivaroxaban (BAY 59-7939), for Thromboprophylaxis After Total Hip Replacement", Circulation, 2006, vol. 114, pp. 2374-2381.

Offermanns S., "Activation of Platelet Function Through G Protein-Coupled Receptors", Circulation Research, 2006, vol. 99, pp. 1293-1304.

Cohen M. et al., "Randomized, Double-Blind, Dose-Ranging Study of Otamixaban, a Novel, Parenteral, Short-Acting Direct Factor Xa Inhibitor, in Percutaneous Coronary Intervention", Circulation, 2007, vol. 115, pp. 2642-2651.

Luo S-Z. et al., "Glycoprotein Ibα Forms Disulfide Bonds with 2 Glycoprotein Ibβ Subunits in the Resting Platelet", Blood, 2007, vol. 109, No. 2, pp. 603-609.

Turpie A. G.G., "Oral, Direct Factor Xa Inhibitors in Development for the Prevention and Treatment of Thromboembolic Diseases", Arterioscler Thromb Vasc Biol., 2007, vol. 27, pp. 1238-1247.

Ansell J. et al., "Pharmacology and Management of the Vitamin K Antagonists", Chest, 2008, vol. 133, pp. 160S-198S.

Peters R. J.G. et al., "The role of fondaparinux as an adjunct to thrombolytic therapy in acute myocardial infarction: a subgroup analysis of the OASIS-6 Trial", European Heart Journal, 2008, vol. 29, pp. 324-331.

Braun A. et al., "Orai1 (CRACM1) is the platelet SOC channel and essential for pathological thrombus formation", Blood, 2009, vol. 113, pp. 2056-2063.

May F. et al., "CLEC-2 is an Essential Platelet-Activating Receptor in Hemostasis and Thrombosis", Blood, 2009, vol. 114, No. 16, pp. 3464-3472.

Nieswandt B. et al., "Integrins in Platelet Activation", Journal of Thrombosis and Haemostasis, 2009, vol. 7, Supplemental 1, pp. 206-209.

Pleines I. et al., "Rac1 is essential for phospholipase C-γ2 activation in platelets", Eur J Physiol, 2009, vol. 457, pp. 1173-1185.

Schellenberger V. et al., "A recombinant polypeptide extends the in vivo half-life of peptides and proteins in a tunable manner", Nature Biotechnology, 2009, vol. 27, No. 12, pp. 1186-1190.

Schroder J. et al., "Deficiency of the Tetraspanin CD63 Associated with Kidney Pathology but Normal Lysosomal Function", Molecular and Cellular Biology, 2009, vol. 29, No. 4, pp. 1083-1094.

Varga-Szabo D. et al., "Calcium Signaling in Platelets", Journal of Thrombosis and Haemostasis, 2009, vol. 7, pp. 1057-1066.

International Search Report and Written Opinion, PCT/EP2016/082629, dated Mar. 21, 2017, 19 pages.

European Search Report for EP 15202530.0, dated Mar. 21, 2016, 7 pages.

International Preliminary Report on Patentability, PCT/EP2016/082629, dated Jul. 5, 2018, 12 pages.

* cited by examiner

Tail bleeding time: WT + soluble human GPV

SOLUBLE GLYCOPROTEIN V FOR TREATING THROMBOTIC DISEASES

This application is the United States national stage entry under 35 U.S.C. § 371 of International Application No. PCT/EP2016/082,629, filed on Dec. 23, 2016 and published as WO 2017/109,212 A1, which claims priority to European Patent Application No. 15202530.0, filed on Dec. 23, 2015. The contents of these applications are each incorporated herein by reference in their entirety.

BACKGROUND

Platelet activation and subsequent thrombus formation at sites of vascular injury is crucial for normal hemostasis, but it can also cause myocardial infarction and stroke (Coughlin S R. *Nature*. 2000; 407: 258-64). Platelet adhesion and activation is a multistep process involving multiple platelet receptor-ligand interactions. Upon vessel wall injury, circulating platelets are rapidly decelerated by transient interactions of the glycoprotein (GP) Ib-V-IX complex with von Willebrand factor (vWF) immobilized on the exposed subendothelial extracellular matrix (e.g. on collagen) (Shapiro M J, et al. *The Journal of Biological Chemistry*. 2000; 275: 25216-21). This interaction retains platelets close to the vessel wall and facilitates the contact between GPVI and collagen (Nieswandt B, et al. *Blood*. 2003; 102: 449-61). GPVI-collagen interactions induce an intracellular signaling cascade leading to platelet activation and the release of secondary platelet agonists, such as thromboxane $A_2$ ($TxA_2$) and adenosine diphosphate (ADP). These soluble agonists together with locally produced thrombin further contribute to platelet activation through G protein ($G_i$, $G_q$, $G_{12/13}$) coupled receptors (Offermanns S. *Circulation research*. 2006; 99: 1293-304). All these signaling pathways synergize to induce complex cellular responses, such as activation of integrins, release of granule contents and the provision of a pro-coagulant surface for the activation of the coagulation cascade (Nakanishi-Matsui M, et al. *Nature*. 2000; 404: 609-13; Cunningham M A, et al. *The Journal of experimental medicine*. 2000; 191: 455-62). The final thrombus is embedded in a fibrin network to withstand the shear forces generated by the flowing blood. The stabilization of a newly formed thrombus is essential to arrest bleeding at sites of vascular injury. However, if this process occurs in an uncontrolled manner it may also lead to thrombotic events causing life-threatening disease states such as myocardial infarction or ischemic stroke. Consequently, antiplatelet and anticoagulant drugs, used alone or in combination, are of major importance in treating cardio- and cerebrovascular diseases (May F, et al. *Blood*. 2009; 114: 3464-72; Schroder J, et al. *Mol Cell Biol*. 2009; 29: 1083-94; Braun A, et al. *Blood*. 2009; 113: 2056-63). Whilst current anti-platelet therapies reduce the recurrence of vascular events, the increased risk of bleeding due to platelet inhibition is a particular concern for patients who have experienced stroke, and a further subset of patients remain refractory to anti-platelet approaches (Pleines I, et al. *Pflugers Archiv: European journal of physiology*. 2009; 457: 1173-85), underscoring the need for novel anti-platelet strategies.

Their central role in platelet adhesion puts two receptor complexes in the focus of platelet research: i) the GPIb-V-IX complex which interacts with vWF immobilized on the injured vessel wall or on activated platelets and thereby recruits platelets from blood stream to the reactive surface under conditions of elevated shear. ii) GPIIb/IIIa (integrin αIIbβ3), a receptor for fibrinogen and vWF that requires inside-out activation mediated by agonist receptors, contributes to firm shear-resistant platelet adhesion and is essential for aggregate formation. The GPIb-V-IX complex is composed of 4 related transmembrane GPs: GPIbα, GPIbβ, GPV and GPIX, which are associated in a stoichiometry of 2:4:2:1 (Luo S-Z et al. *Blood*. 2007; 109(2): 603-9). Within this complex, GPIbα and GPIbβ are disulfide-linked and noncovalently associated with GPIX. GPV is noncovalently associated with GPIb-IX (Nieswandt B, et al. *Journal of Thrombosis and Haemostasis*. 2009; 7: 206-9). Approximately 30,000 copies of the GPIb-IX complex are found on the surface of human platelets (Varga-Szabo D, et al. *Journal of Thrombosis and Haemostasis*. 2009; 7: 1057-66). Loss of GPIb-V-IX function causes Bernard-Soulier syndrome (BSS), a severe bleeding disorder. BSS is characterized by abnormal, giant circulating platelets with defective adhesion to vWF and reduced thrombin responsiveness (Canobbio I, et al. *Cellular signalling*. 2004; 16: 1329-44). While lack or dysfunction of GPIb or GPIX are associated with BSS, no loss of function mutation in GP5 has been reported and the lack of GPV in mice does not lead to a BSS-phenotype (Ramakrishnan V, et al. *PNAS*. 1999; 96: 13336-41; Kahn M L, et al. *Blood*. 1999; 94: 4112-21). GPV is the only subunit which is not required for the correct expression of the complex (Dong J, et al. *Journal of Biological Chemistry*. 1998; 273: 31449-54). WO 95/02054 A2, U.S. Pat. No. 6,005,089 and Lanza F, et al. *Journal of Biological Chemistry*. 1993; 268: 20801-20807 disclose the sequence and structure of the human GPV gene and the amino acid sequence of human GPV. GPV is highly glycosylated and contains a thrombin cleavage site leading to quantitative removal of GPV from the platelet surface and the generation of soluble GPV (sGPV) in the presence of thrombin (Ravanat C, et al. *Blood*. 1997; 89: 3253-62; Azorsa D O, et al. *Thrombosis and Haemostasis*. 1999; 81: 131-8; White G C, et al. *Thrombosis Research*. 38: 641-648). The soluble human GPV generated by thrombin cleavage has the amino acid sequence as shown in SEQ ID NO:10. Of note, this thrombin cleavage site is conserved in the mouse, rat and human protein (Ravanat C, et al. *Blood*. 1997; 89: 3253-62). However, in contrast to protease-activated receptor (PAR) 4-deficient mice, which do not respond upon thrombin stimulation (Kahn M L, et al. *Blood*. 1999; 94: 4112-21; Kahn M L, et al. *Nature*. 1998; 394: 690-4), Gp5$^{-/-}$ mice display grossly normal platelet functionality. Besides thrombin, GPV can, like GPIbα or GPVI, be cleaved by sheddases of the 'a disintegrin and metalloproteinase' (ADAM) family, most notably ADAM17 (also referred to as the tumor necrosis factor-converting enzyme, TACE) and ADAM10 (Garton K J, et al. *Journal of Biological Chemistry*. 2001; 276: 37993-8001; Gardiner E E, et al. *Blood*. 2004; 104: 3611-7; Bergmeier W, et al. *Thrombosis and Haemostasis*. 2004; 91: 951-8), which results in a slightly longer variant of sGPV. However, thrombin is considered as the major regulator of GPV surface expression. SGPV levels differ enormously between plasma and serum (17.3±6.3 ng/ml vs. 1.2±0.17 µg/ml, respectively) (Azorsa D O, et al. *Thrombosis and Haemostasis*. 1999; 81: 131-8) and sGPV levels are slightly elevated under certain pathological conditions, such as ischemic stroke (39.4 ng/ml compared to 28.1 ng/ml in controls) (Wolff V, et al. *Stroke*. 2005; 36: e17-9). To date, no role for sGPV in thrombosis or hemostasis has been described.

SUMMARY OF THE INVENTION

The inventors surprisingly found that soluble GPV has an antithrombotic effect, without affecting the bleeding time.

Thus, the present invention provides an antithrombotic agent comprising soluble GPV. The present invention relates to the following embodiments (1) to (36):

(1) A soluble polypeptide comprising a modified glycoprotein V (GPV) for use in the treatment and/or prevention of a thrombotic disease in a subject, said treatment and/or prevention comprising administering to the subject an effective amount of said soluble polypeptide.

(2) The soluble polypeptide for use according to item (1), wherein the thrombotic disease is selected from the group consisting of thrombo-inflammatory conditions, venous thrombosis, arterial thrombosis, capillary thrombosis, portal vein thrombosis, renal vein thrombosis, jugular vein thrombosis, cerebral venous sinus thrombosis, thrombus formation during or after contacting blood with an artificial surface, in particular extracorporeal membrane oxygenation (ECMO), atherosclerosis, arthritis, coagulopathy, deep venous thrombosis (DVT), disseminated intravascular coagulopathy (DIC), a chronic or acute thromboembolism, pulmonary thromboembolism, Budd-Chiari syndrome, Paget-Schroetter diseases, stroke and myocardial infraction.

(3) The soluble polypeptide for use according to any one of the preceding items, wherein said modified GPV is a truncated GPV.

(4) The soluble polypeptide for use according to any one of the preceding items, wherein said modified GPV or truncated GPV consists of a fragment of the extracellular domain of a native GPV, said fragment having a length of at least 6 amino acids.

(5) The soluble polypeptide for use according to any one of the preceding items, wherein said modified GPV or truncated GPV consists of a fragment of the extracellular domain of a native GPV, said fragment having a length of at least 8 amino acids.

(6) The soluble polypeptide for use according to any one of the preceding items, wherein said modified GPV or truncated GPV consists of a fragment of the extracellular domain of a native GPV, said fragment having a length of at least 30 amino acids.

(7) The soluble polypeptide for use according to any one of the preceding items, wherein said modified GPV or truncated GPV consists of a fragment of the extracellular domain of a native GPV, said fragment having a length of at least 100 amino acids.

(8) The soluble polypeptide for use according to any one of the preceding items, wherein said modified GPV or truncated GPV consists of a fragment of the extracellular domain of a native GPV, said fragment having a length of at least 250 amino acids.

(9) The soluble polypeptide for use according to any one of the preceding items, wherein said modified GPV or truncated GPV consists of a fragment of the extracellular domain of a native GPV, said fragment having a length of at least 400 amino acids.

(10) The soluble polypeptide for use according to any one of items (4) to (9), wherein said fragment has anti-thrombotic activity.

(11) The soluble polypeptide for use according to any one of items (4) to (10), wherein said fragment does not substantially affect bleeding time upon administration.

(12) The soluble polypeptide for use according to any one of items (4) to (11), wherein said native GPV consists of the amino acid sequence as shown in SEQ ID NO:3, and the extracellular domain substantially consists of amino acids 1-503 of SEQ ID NO:3.

(13) The soluble polypeptide for use according to any one of items (4) to (11), wherein said native GPV consists of the amino acid sequence as shown in SEQ ID NO:7, and the extracellular domain substantially consists of amino acids 1-502 of SEQ ID NO:7.

(14) The soluble polypeptide for use according to any one of the preceding items, wherein said soluble polypeptide is a non-naturally occurring polypeptide.

(15) The soluble polypeptide for use according to item (14), further comprising a half-life-extending moiety.

(16) The soluble polypeptide for use according to item (15), wherein said half-life-extending moiety is conjugated to said modified GPV, either directly or via a linker.

(17) The soluble polypeptide for use according to item (16), wherein said half-life-extending moiety is selected from the group consisting of hydroxyethyl starch (HES), polyethylene glycol (PEG), polysialic acids (PSAs) and albumin binding ligands, e.g. fatty acid chains.

(18) The soluble polypeptide for use according to item (15), wherein said half-life-extending moiety is a heterologous amino acid sequence fused to said modified GPV, either directly or via a linker.

(19) The soluble polypeptide for use according to item (18), wherein the half-life extending heterologous amino acid sequence comprises or consists of a polypeptide selected from the group consisting of albumin and a fragment thereof having a length of at least 100 amino acids, immunoglobulin constant regions and fragments thereof, e.g. the Fc fragment, transferrin and fragments thereof, the C-terminal peptide of human chorionic gonadotropin, solvated random chains with large hydrodynamic volume (XTEN), homo-amino acid repeats (HAP), proline-alanine-serine repeats (PAS), afamin, alpha-fetoprotein, Vitamin D binding protein, polypeptides capable of binding under physiological conditions to albumin or immunoglobulin constant regions, and combinations thereof.

(20) The soluble polypeptide for use according to any one of the preceding items, wherein said soluble polypeptide is obtainable by recombinant expression in eukaryotic cells.

(21) The soluble polypeptide for use according to item (20), wherein said eukaryotic cells are mammalian cells.

(22) The soluble polypeptide for use according to item (21), wherein said mammalian cells are CHO cells.

(23) The soluble polypeptide for use according to item (20), wherein said eukaryotic cells are insect cells, e.g. Sf9 cells.

(24) The soluble polypeptide for use according to any one of items (1) to (19), wherein said soluble polypeptide is obtainable by recombinant expression in prokaryotic cells, e.g. in bacterial cells.

(25) The soluble polypeptide for use according to any one of the preceding items, wherein said soluble polypeptide has anti-thrombotic activity.

(26) The soluble polypeptide for use according to any one of the preceding items, wherein said soluble polypeptide does not substantially affect bleeding time upon administration.

(27) The soluble polypeptide for use according to any one of the preceding items, wherein said treatment and/or prevention further comprises administering to said subject an antiplatelet or an anticoagulant drug.

(28) A pharmaceutical composition comprising a soluble polypeptide as defined in any one of items (1) to (26), and a pharmaceutically acceptable excipient.

(29) The pharmaceutical composition of item (28), wherein the soluble polypeptide does not consist of the amino acid sequence as shown in SEQ ID NO:10.

(30) A method of treating a thrombotic disease in a subject, comprising administering to the subject an effective amount of a soluble polypeptide as defined in any one of items (1) to (26), or the pharmaceutical composition of item (28) or (29).

(31) A method of preparing the soluble polypeptide according to any one of items (1) to (26), comprising expressing a nucleic acid encoding the soluble polypeptide as defined in any one of items (1) to (26) in a mammalian cell, and recovering the soluble polypeptide from the culture medium.

(32) A non-naturally occurring soluble GPV as defined in any one of items (5) to (26).

(33) The non-naturally occurring soluble GPV of item (32), which does not consist of the amino acid sequence as shown in SEQ ID NO:10.

(34) A soluble GPV which does not consist of the amino acid sequence as shown in SEQ ID NO:10.

(35) A pharmaceutical kit comprising (i) a soluble polypeptide according to any one of items (1) to (26), and (ii) an antiplatelet or an anticoagulant drug other than said soluble polypeptide.

(36) The pharmaceutical kit of item (35), wherein the soluble polypeptide does not consist of the amino acid sequence as shown in SEQ ID NO:10.

DETAILED DESCRIPTION

Figure 1:
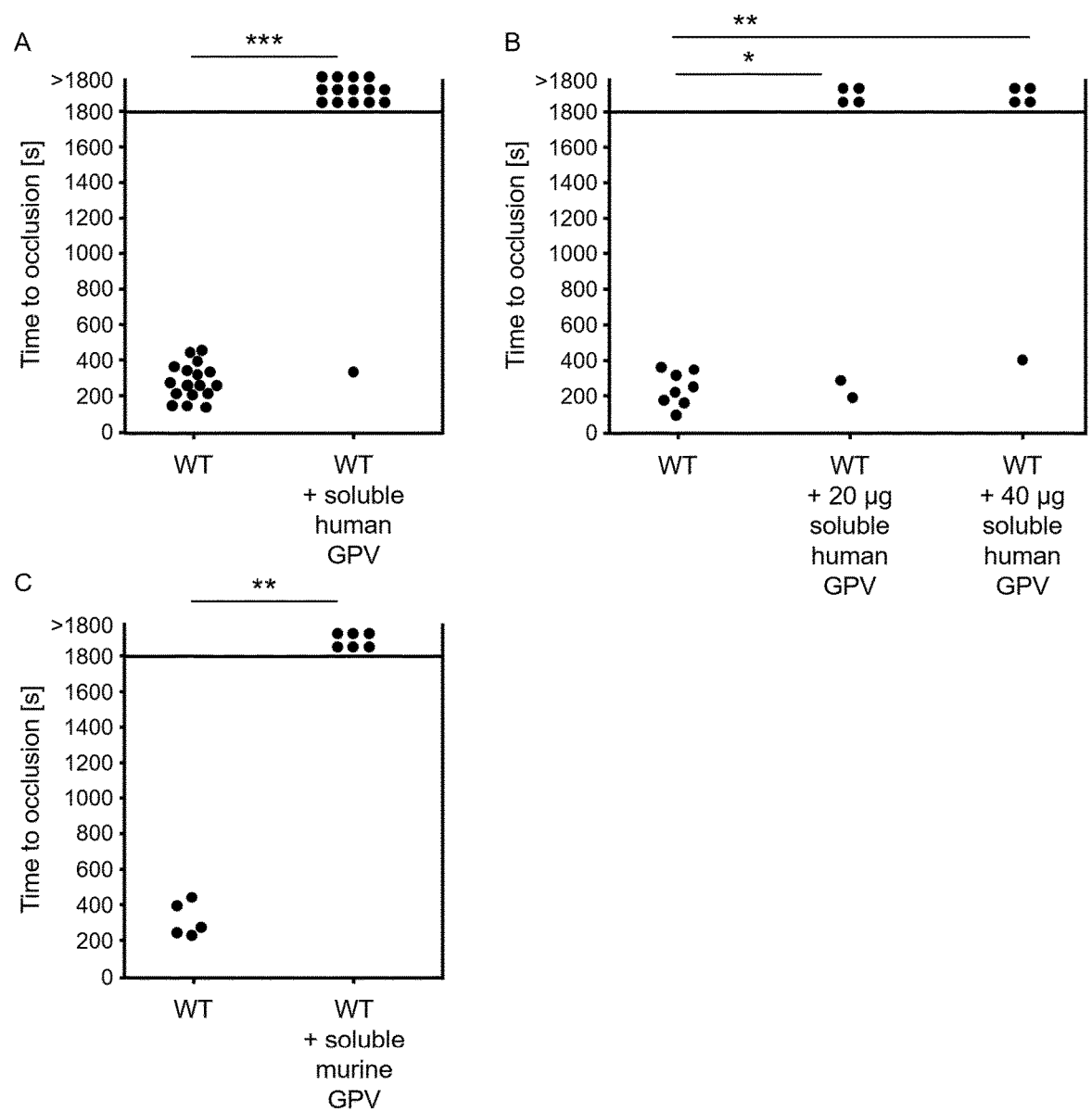
FIG. 1: Soluble GPV has an antithrombotic effect in an aortic injury model. The abdominal aorta was mechanically injured by a single firm compression with a forceps and blood flow was monitored with a Doppler flowmeter. Time to final occlusion is shown. A,B) Occlusion times after injection of soluble human GPV (A: shGPV; B: shGPV-Albumin-Fusion-Protein (AFP)) or soluble murine GPV (C: smGPV). Each symbol represents one individual mouse. In cases where mice were unable to form occlusive thrombi Fisher's exact test was used to calculate P-values. * P<0.05;  P<0.01; * P<0.001

The present invention relates to a soluble polypeptide comprising a modified glycoprotein V (GPV) lacking a functional transmembrane domain for use in the treatment or prevention of a thrombotic disease in a subject, said treatment or prevention comprising administering to the subject an effective amount of said soluble polypeptide. Preferably, the modified GPV is a truncated GPV.

The term "soluble" as used herein refers to a polypeptide that is not bound to a cell membrane. In particular, a soluble polypeptide is not integrated into a cell membrane via a transmembrane domain and/or it is incapable of being integrated into a cell membrane via a transmembrane domain. Typically, the soluble polypeptide lacks a functional transmembrane domain. Preferably, soluble polypeptides are soluble in water or a buffer, such as PBS.

Glycoprotein V

The term "Glycoprotein V" or "GPV", as used herein, denotes a protein having a sequence identity of at least 50% to the amino acid sequence as shown in SEQ ID NO:3. Preferably, the GPV has an amino acid identity of at least 60%, or at least 70%, or at least 80%, or at least 90%, or at least 95% to the amino acid sequence as shown in SEQ ID NO:3. In accordance with the present invention, a sequence being evaluated (the "Compared Sequence") has a certain "percent identity with," or is a certain "percent identical to" a claimed or described sequence (the "Reference Sequence") after alignment of the two sequences. The "Percent Identity" is determined according to the following formula:

$$\text{Percent Identity} = 100[1-(C/R)]$$

In this formula, C is the number of differences between the Reference Sequence and the Compared Sequence over the length of alignment between the two sequences wherein (i) each base in the Reference Sequence that does not have a corresponding aligned base in the Compared Sequence, and (ii) each gap in the Reference Sequence, and (iii) each aligned base in the Reference Sequence that is different from an aligned base in the Compared Sequence constitutes a difference. R is the number of bases of the Reference Sequence over the length of the alignment with the Compared Sequence with any gap created in the Reference Sequence also being counted as a base.

If an alignment exists between the Compared Sequence and the Reference Sequence for which the Percent Identity (calculated as above) is about equal to, or greater than, a specified minimum, the Compared Sequence has that specified minimum Percent Identity even if alignments may exist elsewhere in the sequence that show a lower Percent Identity than that specified.

In a preferred embodiment, the length of aligned sequence for comparison purposes is at least 30%, preferably at least 40%, more preferably at least 50%, even more preferably at least 60%, and even more preferably at least 70%, 80%, or 90% of the length of the Reference Sequence.

The comparison of sequences and determination of percent identity (and percent similarity) between two amino acid sequences can be accomplished using any suitable program, e.g. the program "BLAST 2 SEQUENCES (blastp)" (Tatusova et al. *FEMS Microbiol. Lett.* 1999. 174: 247-250) with the following parameters: Matrix BLOSUM62; Open gap 11 and extension gap 1 penalties; gap x_dropoff 50; expect 10.0 word size 3; Filter: none. According to the present invention, the sequence comparison covers at least 40 amino acids, preferably at least 80 amino acids, more preferably at least 100 amino acids, and most preferably at least 120 amino acids.

Typically, the GPV is platelet GPV, and the modified GPV is modified platelet GPV.

Native (i.e. non-modified) GPV comprises a functional transmembrane domain, i.e. it comprises an amino acid sequence capable of conferring integration into a cell membrane (e.g. a plasma membrane) during expression.

The native GPV is a naturally occurring GPV. Preferably, the native GPV is of mammalian origin. In one embodiment, the GPV is a human GPV. According to this embodiment, the native GPV preferably comprises or consists of the amino acid sequence as shown in SEQ ID NO:3. In another embodiment, the native GPV is a murine GPV. According to this embodiment, the native GPV preferably comprises or consists of the amino acid sequence as shown in SEQ ID NO:7. The term native GPV as used herein includes, but is not limited to, homologs and orthologs of human GPV represented by SEQ ID NO:2 (with signal peptide) and SEQ ID NO:3 (without signal peptide). Unless indicated otherwise, the term GPV refers to the mature polypeptide lacking the signal peptide.

Most preferably, the native GPV comprises or consists of the amino acid sequence as shown in SEQ ID NO:3.

Modified GPV

The modified GPV in accordance with this invention differs from the native GPV from which it is derived (also referred to as the "parent GPV" or "non-modified GPV") at least in that the transmembrane domain is no longer functional, due to mutation or any other means. For example, the amino acid sequence representing the transmembrane domain in the modified GPV may have one or more substitutions, deletions and/or insertions relative to the parent GPV. In one embodiment, the amino acid sequence of the modified GPV lacks at least the entire transmembrane domain of the parent GPV. In another embodiment, the modified GPV is a truncated GPV. The transmembrane domain of human GPV extends from amino acids positions 504 to 527 of SEQ ID NO:3. The transmembrane domain of murine GPV extends from amino acids positions 503 to 526 of SEQ ID NO:7.

1, 2, 3, 4, 5, 6, 7, 8, 9, 10, 11, 12, 13, 14, 15, 16, 17, 18, 19, 20, 21, 22, 23 or 24 amino acids of the transmembrane domain of the GPV may be deleted or substituted in the modified GPV. In one embodiment, 1, 2, 3, 4, 5, 6, 7, 8, 9, 10, 11, 12, 13, 14, 15, 16, 17, 18, 19, 20, 21, 22, 23 or 24 amino acids of the transmembrane domain of human GPV (amino acids 504 to 527 of SEQ ID NO:3) may be deleted or substituted. In another embodiment, 1, 2, 3, 4, 5, 6, 7, 8, 9, 10, 11, 12, 13, 14, 15, 16, 17, 18, 19, 20, 21, 22, 23 or 24 amino acids of the transmembrane domain of murine GPV (amino acids 503 to 526 of SEQ ID NO:7) may be deleted or substituted.

The modified GPV, preferably the truncated GPV, has antithrombotic activity. Antithrombotic activity can be determined as shown in the experiment described in Example 1 (See also "Mechanical Injury of the Abdominal Aorta" in the "Materials and Methods" section of the Examples). There is antithrombotic activity if the tested compound (e.g. 20 μg) is capable of delaying or preventing arterial occlusive thrombus formation in mice. Preferably, the arterial occlusive thrombus formation is delayed by at least 1 minute, more preferably by at least 5 minutes, most preferably by at least 10 minutes.

Truncated GPV

A truncated GPV consists of a fragment of GPV. The truncation typically is at the C-terminal end of the GPV. The N-terminal end may be truncated, or it may not be truncated.

The fragment of GPV has a length of at least 6 amino acids. Preferably, the length of the GPV fragment is at least 7, at least 8, at least 9, at least 10, at least 15, at least 20, at least 50, at least 100, at least 200, at least 300, or at least 400 amino acids. In certain embodiments, the truncated GPV consists of a fragment of the amino acid sequence as shown in SEQ ID NO:3, wherein said fragment has a minimum length of 6 amino acids, preferably of at least 7, at least 8, at least 9, at least 10, at least 15, at least 20, at least 50, at least 100, at least 200, at least 300, or at least 400 amino acids.

In one embodiment, the truncated GPV has a C-terminal truncation and lacks the complete transmembrane domain of the GPV from which it is derived. In another embodiment, the truncated GPV has a C-terminal truncation and lacks the transmembrane domain to such an extent that the truncated GPV is not membrane-bound.

Preferred truncated GPVs consist of an amino acid sequence selected from the following amino acid sequences, wherein all amino acid positions refer to SEQ ID NO:3 (embodiments 1-71) or SEQ ID NO:7 (embodiments 72-141), respectively, as indicated:

TABLE 1

| Embodiment No. | from | to |
|---|---|---|
| | | of SEQ ID NO: 3 |
| 1 | 1 | 520 |
| 2 | 2 | 519 |
| 3 | 3 | 518 |
| 4 | 4 | 517 |
| 5 | 5 | 516 |
| 6 | 6 | 515 |
| 7 | 7 | 514 |
| 8 | 8 | 513 |
| 9 | 9 | 512 |
| 10 | 10 | 511 |
| 11 | 11 | 510 |
| 12 | 12 | 509 |
| 13 | 13 | 508 |
| 14 | 14 | 507 |
| 15 | 15 | 506 |
| 16 | 16 | 505 |
| 17 | 17 | 504 |
| 18 | 18 | 503 |
| 19 | 19 | 502 |
| 20 | 20 | 501 |
| 21 | 21 | 500 |
| 22 | 22 | 499 |
| 23 | 23 | 498 |
| 24 | 24 | 497 |
| 25 | 25 | 496 |
| 26 | 26 | 495 |
| 27 | 27 | 494 |
| 28 | 28 | 493 |
| 29 | 29 | 492 |
| 30 | 30 | 491 |
| 31 | 31 | 490 |
| 32 | 32 | 489 |
| 33 | 33 | 488 |
| 34 | 34 | 487 |
| 35 | 35 | 486 |
| 36 | 36 | 485 |
| 37 | 37 | 484 |
| 38 | 38 | 483 |
| 39 | 39 | 482 |
| 40 | 40 | 481 |
| 41 | 41 | 480 |
| 42 | 42 | 479 |
| 43 | 43 | 478 |
| 44 | 44 | 477 |
| 45 | 45 | 476 |
| 46 | 46 | 475 |
| 47 | 47 | 474 |
| 48 | 48 | 473 |
| 49 | 49 | 472 |
| 50 | 50 | 471 |
| 51 | 51 | 470 |
| 52 | 52 | 469 |
| 53 | 53 | 468 |
| 54 | 54 | 467 |
| 55 | 55 | 466 |
| 56 | 56 | 465 |
| 57 | 57 | 464 |

TABLE 1-continued

| Embodiment No. | from | to |
|---|---|---|
| 58 | 58 | 463 |
| 59 | 59 | 462 |
| 60 | 60 | 461 |
| 61 | 61 | 460 |
| 62 | 62 | 459 |
| 63 | 63 | 458 |
| 64 | 64 | 457 |
| 65 | 65 | 456 |
| 66 | 66 | 455 |
| 67 | 67 | 454 |
| 68 | 68 | 453 |
| 69 | 69 | 452 |
| 70 | 70 | 451 |
| 71 | 71 | 450 |
| of SEQ ID NO: 7 | | |
| 72 | 1 | 520 |
| 73 | 2 | 519 |
| 74 | 3 | 518 |
| 75 | 4 | 517 |
| 76 | 5 | 516 |
| 77 | 6 | 515 |
| 78 | 7 | 514 |
| 79 | 8 | 513 |
| 80 | 9 | 512 |
| 81 | 10 | 511 |
| 82 | 11 | 510 |
| 83 | 12 | 509 |
| 84 | 13 | 508 |
| 85 | 14 | 507 |
| 86 | 15 | 506 |
| 87 | 16 | 505 |
| 88 | 17 | 504 |
| 89 | 18 | 503 |
| 90 | 19 | 502 |
| 91 | 20 | 501 |
| 92 | 21 | 500 |
| 93 | 22 | 499 |
| 94 | 23 | 498 |
| 95 | 24 | 497 |
| 96 | 25 | 496 |
| 97 | 26 | 495 |
| 98 | 27 | 494 |
| 99 | 28 | 493 |
| 100 | 29 | 492 |
| 101 | 30 | 491 |
| 102 | 31 | 490 |
| 103 | 32 | 489 |
| 104 | 33 | 488 |
| 105 | 34 | 487 |
| 106 | 35 | 486 |
| 107 | 36 | 485 |
| 108 | 37 | 484 |
| 109 | 38 | 483 |
| 110 | 39 | 482 |
| 111 | 40 | 481 |
| 112 | 41 | 480 |
| 113 | 42 | 479 |
| 114 | 43 | 478 |
| 115 | 44 | 477 |
| 116 | 45 | 476 |
| 117 | 46 | 475 |
| 118 | 47 | 474 |
| 119 | 48 | 473 |
| 120 | 49 | 472 |
| 121 | 50 | 471 |
| 122 | 51 | 470 |
| 123 | 52 | 469 |
| 124 | 53 | 468 |
| 125 | 54 | 467 |
| 126 | 55 | 466 |
| 127 | 56 | 465 |
| 128 | 57 | 464 |
| 129 | 58 | 463 |
| 130 | 59 | 462 |
| 131 | 60 | 461 |
| 132 | 61 | 460 |
| 133 | 62 | 459 |

TABLE 1-continued

| Embodiment No. | from | to |
|---|---|---|
| 134 | 63 | 458 |
| 135 | 64 | 457 |
| 136 | 65 | 456 |
| 137 | 66 | 455 |
| 138 | 67 | 454 |
| 139 | 68 | 453 |
| 140 | 69 | 452 |
| 141 | 70 | 451 |
| 142 | 71 | 450 |

The upper and lower limits of the amino acid sequences of above embodiments can be combined with each other.

In particularly, preferred embodiments of the truncated GPV consists of amino acids 1-516 of SEQ ID NO:3, or of amino acids 1-502 of SEQ ID NO:7.

In other embodiments, the truncated GPV comprises or consist of the following sequences.

TABLE 2

| Embodiment No. | The truncated GPV comprises or consists of the following amino acids of SEQ ID NO: 3 |
|---|---|
| 143 | 1-15 |
| 144 | 16-30 |
| 145 | 31-45 |
| 146 | 46-60 |
| 147 | 61-75 |
| 148 | 76-90 |
| 149 | 91-105 |
| 150 | 106-120 |
| 151 | 121-135 |
| 152 | 136-150 |
| 153 | 151-165 |
| 154 | 166-180 |
| 155 | 181-195 |
| 156 | 196-205 |
| 157 | 211-225 |
| 158 | 226-240 |
| 159 | 241-255 |
| 160 | 256-270 |
| 161 | 271-285 |
| 162 | 286-300 |
| 163 | 301-315 |
| 164 | 316-330 |
| 165 | 331-345 |
| 166 | 346-360 |
| 167 | 361-365 |
| 168 | 376-390 |
| 169 | 391-405 |
| 170 | 406-420 |
| 171 | 421-435 |
| 172 | 436-450 |
| 173 | 451-465 |
| 174 | 466-480 |
| 175 | 481-500 |

In a specific embodiment of the present invention the soluble polypeptide for use as described herein comprises or consists of the amino acid sequence as shown in SEQ ID NO:10.

In another specific embodiment the soluble polypeptide of the invention is a non-naturally occurring polypeptide. In yet another specific embodiment the soluble polypeptide of the invention does not consist of the amino acid sequence as shown in SEQ ID NO:10. In yet another specific embodiment the soluble polypeptide of the invention is a non-naturally occurring polypeptide and does not consist of the amino acid sequence as shown in SEQ ID NO:10.

Further Components of the Polypeptide

The soluble polypeptide of the invention may comprise additional amino acids other than those derived from GPV or other half-life ext In one embodiment of the invention, the half-life of the soluble polypeptide of the invention is extended by chemical modification, e.g. attachment, either directly or via a linker, of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the soluble polypeptide, preferably the modified GPV, is conjugated to a half-life extending protein (HLEP) such as albumin via a chemical linker. The principle of this conjugation technology has been described in an exemplary manner by Conjuchem LLC (see, e.g. U.S. Pat. No. 7,256, 253).

In another embodiment of the invention, the soluble polypeptide comprises a heterologous amino acid sequence, i.e. heterologous to the respective GPV used, which is fused to said GPV either directly or via a linker.

Heterologous sequences may be tag sequences which are recognized by antibodies or other molecules having high affinity to the tag. Examples include, but are not limited to, poly-histidine tags, FLAG tag, myc-tag, GST tag, etc. Tag sequences usually facilitate purification of the polypeptide upon expression in host cells.

In a preferred embodiment, the soluble polypeptide further comprises a half-life extending protein (HLEP). Preferably, the HLEP is an albumin or a fragment thereof. The N-terminus of the albumin may be fused to the C-terminus of the modified GPV. One or more HLEPs may be fused to the N- or C-terminal part of modified GPV provided that they do not interfere with or abolish the anti-thrombotic activity of the modified GPV.

In one embodiment the polypeptide has the following structure:

$$mGPV\text{-}L1\text{-}H, \qquad \text{[formula 1]}$$

wherein mGPV is the modified GPV, L1 is a chemical bond or a linker sequence, and H is a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type GPV. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO2007/090584. In another embodiment of the invention, the peptidic linker between the modified GPV moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g. in WO 2013/120939 A1.

Preferred HLEP sequences are described below. Likewise encompassed by the invention are fusions to the exact "N-terminal amino acid" of the respective HLEP, or fusions to the "N-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of modified GPV in tandem, e.g. as successive repeats.

Half-Life Extending Polypeptides (HLEPs)

Preferably, the half-life extending moiety is a half-life extending polypeptide (HLEP), more preferably HLEP is selected from albumin or fragments thereof, immunoglobulin constant region and fragments thereof, e.g. the Fc fragment, solvated random chains with large hydrodynamic volume (e.g. XTEN (Schellenberger et al. *Nature Biotechnol.* 2009. 27: 1186-1190), homo-amino acid repeats (HAP) or proline-alanine-serine repeats (PAS)), afamin, alpha-fetoprotein, Vitamin D binding protein, transferrin or variants thereof, carboxyl-terminal peptide (CTP) of human chorionic gonadotropin-R subunit, polypeptides or lipids capable of binding under physiological conditions to albumin or immunoglobulin constant region.

A "half-life extending polypeptide" as used herein is preferably selected from the group consisting of albumin, a member of the albumin-family, the constant region of immunoglobulin G and fragments thereof, region and polypeptides capable of binding under physiological conditions to albumin, to members of the albumin family as well as to fragments of an immunoglobulin constant region. It may be a full-length half-life-extending protein described herein (e.g. albumin, a member of the albumin-family or the constant region of immunoglobulin G) or one or more fragments thereof that are capable of stabilizing or prolonging the therapeutic activity or the biological activity of the modified GPV. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP fragment of the proposed coagulation factor insertion constructs of the invention may be a variant of a normal HLEP. The term "variants" includes insertions, deletions and substitutions, either conservative or non-conservative, where such changes do not substantially alter the active site, or active domain which confers the biological activities of the modified GPV.

In particular, the proposed modified GPV-HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin or albumin from other vertebrates or fragments thereof, or analogs or variants of these molecules or fragments thereof.

In particular, the proposed modified GPV fusion constructs of the invention may include naturally occurring polymorphic variants of human albumin and fragments of human albumin.

Generally speaking, an albumin fragment or variant will be at least 10, preferably at least 40, most preferably more than 70 amino acids long.

The albumin fragment of the proposed modified GPV fusion constructs of the invention may comprise at least one subdomain or domain of HA or conservative modifications thereof.

Immunoglobulins as HLEPs

In a preferred embodiment the soluble polypeptide of the invention comprises or consists of the amino acid sequence as shown in SEQ ID NO:9.

Immunoglobulins as HLEPs

Immunoglobulin G (IgG) constant regions (Fc) are known in the art to increase the half-life of therapeutic proteins (Dumont J A, et al. *BioDrugs*. 2006; 20: 151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide fragment is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic proteins in vivo half-lives. US 2004/0087778 and WO 2005/001025 describe fusion proteins of Fc domains or at least fragments of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life extending properties.

In certain embodiments, the Fc fusion protein is monomeric. In other embodiments, the Fc fusion protein is dimeric.

Various HLEPs which can be used in accordance with this invention are described in detail in WO 2013/120939.

Nucleic Acid and Expression

The nucleic acid encoding the polypeptide to be expressed can be prepared according to methods known in the art. Based on the cDNA sequence of human GPV (SEQ ID NO:1) or of murine GPV (SEQ ID NO:5), recombinant DNA encoding the above-mentioned modified GPV constructs can be designed and generated. Further details of the human and mouse sequences are summarized in table 3.

TABLE 3

Details of mouse and human wild-type GPV Sequences

| | Mouse | Human |
|---|---|---|
| Entrez | 14729 | 2814 |
| Ensembl | ENSMUSG00000047953 | ENSG00000178732 |
| Uniprot | Q3TA66 | P40197 |
| mRNA RefSeq | NM_008148 | NM_004488 |
| Protein RefSeq | NP_032174 | NP_004479 |
| Location | Chr 16: 30.23 - 30.23 Mb | Chr 3: 195.6 - 195.6 Mb |
| Molecular Mass [Da] | 63251 | 60828 |

Constructs in which the cDNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g. the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide comprising the modified GPV into mammalian host cells.

Host Cells

Any host cell susceptible to cell culture, and to expression of polypeptides, preferably glycosylated polypeptides, may be utilized in accordance with the present invention. In certain embodiments, the host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (HEK293 or HEK293 cells subcloned for growth in suspension culture, Graham et al., J. Gen Virol., 36:59, 1977); baby hamster kidney cells (BHK, ATCC CCL10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals NY. Acad. Sci., 383:44-68, 1982); MRC 5 cells; PS4 cells; human amniocyte cells (CAP); and a human hepatoma line (Hep G2). Preferably, the cell line is a human or a rodent cell line, especially a hamster cell line such as CHO.

Methods suitable for introducing nucleic acids sufficient to achieve expression of a glycoprotein of interest into mammalian host cells are known in the art. See, for example, Gething, et al., *Nature*. 1981; 293: 620-625; Mantei, et al., *Nature*. 1979; 281: 40-46; Levinson, et al. EP 117,060; and EP 117,058. For mammalian cells, common methods of introducing genetic material into mammalian cells include the calcium phosphate precipitation method of Graham and van der Erb (*Virology*. 1978; 52: 456-457) or the Lipofectamine™ (Gibco BRL) Method of Hawley-Nelson (*Focus*. 1993; 15: 73). General aspects of mammalian host cell system transfections have been described by Axel in U.S. Pat. No. 4,399,216. For various techniques for introducing genetic material into mammalian cells, see Keown et al. (Methods in Enzymology, 1989), Keown et al. (*Methods in Enzymology*. 1990; 185: 527-537), and Mansour et al. (*Nature*, 1988; 336: 348-352).

The basal medium chosen for culturing the host cell line is not critical to the present invention and may be any one of, or combination of, those known to the art which are suitable for culturing mammalian cells. Media such as Dulbecco's Modified Eagle Medium, Ham's F-12 Medium, Eagle's Minimal Essential Medium and RPMI-1640 Medium and the like are commercially available. The addition of growth factors such as recombinant insulin is optional. In one embodiment, the production medium is free of animal-derived components. In a preferred embodiment, the medium is "protein-free" in the sense that it is either completely free of any protein or at least free of any protein that is not recombinantly produced. Human serum albumin may be used as a serum-free culture supplement for the production of the glycoprotein. Optionally, the medium contains a protease inhibitor, such as a serine protease inhibitor, which is suitable for tissue culture and which is of synthetic or vegetable origin.

Generally, the present invention may be used with any cell culture method that is amenable to the expression of glycoproteins. For example, cells may be grown in batch or fed-batch cultures, where the culture is terminated after sufficient expression of the glycoprotein, after which the expressed glycoprotein is harvested. Preferably, cells may be grown in continuous cultures (e.g. perfusion cultures), where fresh medium is periodically or continuously added to the culture, and the expressed glycoprotein is harvested periodically or continuously. The culture can be of any conventional type of culture, such as batch, fed-batch or continuous, but is preferably continuous. Suitable continuous cultures include perfusion culture.

One of ordinary skill in the art will be able to tailor specific cell culture conditions in order to optimize certain characteristics of the cell culture including but not limited to growth rate, cell viability, final cell density of the cell culture, final concentration of detrimental metabolic byproducts such as lactate and ammonium, titer of the expressed glycoprotein, extent and composition of the oligosaccharide side chains or any combination of these or other conditions deemed important by the practitioner.

Isolation of the Expressed Soluble Polypeptide

In general, it will typically be desirable to isolate and/or purify glycoproteins expressed according to the present invention. In certain embodiments, the expressed glycoprotein is secreted into the medium and thus cells and other solids may be removed, as by centrifugation or filtering for example, as a first step in the purification process.

The expressed glycoprotein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (see, e.g. Scopes, Protein Purification Principles and Practice 2nd Edition, Springer-Verlag, New York, 1987; Higgins S J and Hames B D (eds.), Protein Expression: A Practical Approach, Oxford Univ Press, 1999; and Deutscher M P, Simon M I, Abelson J N (eds.), Guide to Protein Purification: Methods in Enzymology (Methods in Enzymology Series, Vol. 182), Academic Press, 1997, each of which is incorporated herein by reference). For immunoaffinity chromatography in particular, the glycoprotein may be isolated by binding it to an affinity column comprising antibodies that were raised against that glycoprotein and were affixed to a stationary support. Alternatively, affinity tags such as an influenza coat sequence, poly-histidine, or glutathione-S-transferase can be attached to the glycoprotein by standard recombinant techniques to allow for easy purification by passage over the appropriate affinity column. If the soluble GPV to be purified comprises a HLEP, antibodies directed against the HLEP, or other compounds capable of binding to the HLEP can be affixed to an affinity column so as to perform affinity chromatography. Protease inhibitors such as phenyl methyl sulfonyl fluoride (PMSF), leupeptin, pepstatin or aprotinin may be added at any or all stages in order to reduce or eliminate degradation of the glycoprotein during the purification process. Protease inhibitors are particularly advantageous when cells must be lysed in order to isolate and purify the expressed glycoprotein. Additionally or alternatively, glycosidase inhibitors may be added at any or all stages in order to reduce or eliminate enzymatic trimming of the covalently attached oligosaccharide chains.

One of ordinary skill in the art will appreciate that the exact purification technique will vary depending on the character of the polypeptide to be purified, the character of the cells from which the polypeptide is expressed, and/or the composition of the medium in which the cells were grown.

Compositions and Kits

Another aspect of the invention is a pharmaceutical composition comprising soluble polypeptide of the invention, and a pharmaceutically acceptable excipient or carrier. The pharmaceutical composition may comprise a soluble polypeptide in an effective amount for treating or preventing a thrombotic disease in a subject. The pharmaceutical composition may comprise about 10 μg-1,000 mg, preferably about 100 μg-500 mg, more preferably 1 mg-100 mg of the soluble polypeptide. The pharmaceutical composition may comprise about 0.01-20,000 μg/ml, preferably about 0.1-1000 μg/ml, more preferably 0.5-500 μg/ml, most preferably about 100 μg/ml of the soluble polypeptide. The pharmaceutical composition may further comprise a pharmaceutically acceptable carrier or diluent. Carriers and diluents suitable in the pharmaceutical composition are well known in the art.

Therapeutic formulations of the glycoproteins of the invention suitable in the methods described herein can be prepared for storage as lyophilized formulations or aqueous solutions by mixing the glycoprotein having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives, see, Remington's Pharmaceutical Sciences, 16th edition (Osol, ed.) 1980. Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g. monosodium citrate-disodium citrate mixture, citric acid-trisodium citrate mixture, citric acid-monosodium citrate mixture, etc.), succinate buffers (e.g. succinic acid-monosodium succinate mixture, succinic acid-sodium hydroxide mixture, succinic acid-disodium succinate mixture, etc.), tartrate buffers (e.g. tartaric acid-sodium tartrate mixture, tartaric acid-potassium tartrate mixture, tartaric acid-sodium hydroxide mixture, etc.), fumarate buffers (e.g. fumaric acid-monosodium fumarate mixture, fumaric acid-disodium fumarate mixture, monosodium fumarate-disodium fumarate mixture, etc.), gluconate buffers (e.g. gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g. lactic acid-sodium lactate mixture, lactic acid-sodium hydroxide mixture, lactic acid-potassium lactate mixture, etc.) and acetate buffers (e.g. acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g. chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polyhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g. starch), chelating agents (e.g. EDTA), antioxidants (e.g. ascorbic acid, methionine, vitamin E), and cosolvents. The pharmaceutical composition may have a pH of about 5.0-10.0, preferably about 5.6-9.0, more preferably about 6.0-8.8, most preferably about 6.5-8.0. For example, the pH may be about 6.2, 6.5, 6.75, 7.0, or 7.5.

The pharmaceutical compositions of the present invention may be formulated for oral, sublingual, intranasal, intraocular, rectal, transdermal, mucosal, topical or parenteral administration. Parenteral administration may include intradermal, subcutaneous, intramuscular (i.m.), intravenous (i.v.), intraperitoneal (i.p.), intra-arterial, intramedullary, intracardiac, intraarticular (joint), intrasynovial, intracranial, intraspinal, and intrathecal (spinal fluids) injection or infusion, preferably intraperitoneal (i.p.) injection in mouse and intravenous (i.v.) or subcutaneous (s.c.) in human. Any device suitable for parenteral injection or infusion of drug formulations may be used for such administration. For example, the pharmaceutical composition may be contained in a sterile pre-filled syringe.

Another aspect of the present invention is a pharmaceutical kit comprising (i) a soluble polypeptide as defined hereinabove and (ii) an anticoagulant or antiplatelet drug other than said soluble polypeptide. In one embodiment, the soluble polypeptide and the anticoagulant or antiplatelet drug are contained in separate compositions.

The term "anticoagulant or antiplatelet drug" refers to heparins, direct thrombin inhibitors (DTI), direct or selective Factor Xa inhibitors (xaban) and vitamin K antagonists (VKA). Thus, "anticoagulant or antiplatelet drugs" can include natural occurring or synthetic heparins. The term "anticoagulant or antiplatelet drug" also meant to include substances that prevent coagulation of blood by inhibiting directly or selective thrombin or Factor Xa. In another embodiment, the anticoagulant substance is a vitamin K antagonist.

In some embodiments the anticoagulant or antiplatelet drug is selected from
  (i) a heparin, in particular a unfractionated heparin (UFH) or a low-molecular-weight heparin (LMWH),
  (ii) a direct thrombin inhibitor (DTI), in particular dabigatran, melagatran, argatroban, hirudin, lepirudin, bivalirudin, ximelagatran or desirudin (Di Nisio et al. *N Engl J Med.* 2005; 353: 1028-40),
  (iii) a direct or selective Factor Xa inhibitor (xaban), in particular rivaroxaban (Eriksson et al., *Circulation.* 114: 2374-81), apixaban (*Arterioscler. Thromb. Vasc. Biol.* 27: 1238-47), betrixaban, edoxaban, otamixaban (Cohen et al., *Circulation* 115: 2642-51) or fondaparinux (Peters et al., *Eur. Heart J.* 29: 324-31) and,
  (iv) a vitamin K antagonist (VKA), in particular phenprocoumon, acenocoumarol or warfarin and related 4-hydroxycoumarin-containing molecules, coumatetralyl, dicoumarol, ethyl biscoumacetate, clorindione, diphenandione, phenandione or tioclomarol (see e.g. Ansell et al. 2008, "Pharmacology and management of the vitamin K antagonists", American College of Chest Physicians Evidence-Based Clinical Practice Guidelines (8th Edition). Chest 133 (6 Suppl): 160S-198S).

Another aspect of the present invention is a pharmaceutical kit comprising (i) a soluble polypeptide as defined hereinabove and (ii) an antiplatelet or anticoagulant drug other than said soluble polypeptide, for simultaneous, separate or sequential use in the treatment of a thrombotic disease.

Treatment of Thrombotic Disease

The soluble polypeptide of the invention can be used for treating or preventing thrombotic diseases.

A "thrombotic disorder" or "thrombotic disease" used herein is any disorder or disease characterized by the formation of a thrombus (blood clot) that obstructs or decreases blood flow. The thrombus may remain local to where it formed, or it may detach to occlude blood flow downstream (thromboembolism). In some embodiments, a thrombosis may occur in a vein (venous thrombosis) or in an artery (arterial thrombosis) anywhere in the body, including the heart and brain. When the thrombosis occurs in the coronary circulation, it is referred to as a coronary thrombosis. When the thrombosis occurs in the cerebral circulation, it is referred to as a cerebral thrombosis.

A thrombotic disorder can include a venous, arterial, or capillary thrombosis, thrombus formation in the heart, chronic and/or acute thromboembolism (e.g. pulmonary embolism, cerebral thromboembolism following atrial fibrillation-induced thrombus formation (e.g. stroke prevention in atrial fibrillation (SPAF)), thrombus formation as a result of contacting the blood of a human or animal subject with an artificial surface (e.g. in patients with valve replacements, in particular a mechanical heart valve, stents, percutaneous coronary intervention (PCI), extracorporeal membrane oxygenation (ECMO), or undergoing cardiopulmonary bypass surgery (CPB surgery)). The thrombus can cause or increase the risk of a stroke, acute ischemic stroke, myocardial infarction, unstable angina, deep vein thrombosis (DVT), portal vein thrombosis, thromboembolism, renal vein thrombosis, jugular vein thrombosis, cerebral venous sinus thrombosis, Budd-Chiari syndrome, Paget-Schroetter diseases, or silent brain ischemia (SBI). A thrombotic disease in accordance with this invention may further include pulmonary embolism, atherosclerosis, factor V Leiden, antithrombin III deficiency, protein C deficiency, protein S deficiency, prothrombin gene mutation (G20210A), hyperhomocysteinemia, antiphospholipid antibody syndrome, anticardiolipin antibody, thrombosis syndrome, lupus anticoagulant syndrome, malignancy, major surgery, immobilization, oral contraceptive use, thalidomide use, especially in combination with dexamethasone, heparin-induced thrombocytopenia, pregnancy, myeloproliferative disorders, inflammatory bowel disease, nephrotic syndrome, paroxysmal nocturnal hemoglobinuria, hyperviscosity syndrome, Waldenstrom's macroglobulinemia, and trauma. The term thrombotic disease also refers to thrombosis induced by cancer, e.g. multiple myeloma and other hematologic cancers, adenocarcinoma, cancer of the pancreas, stomach, ovaries, prostate, colon, lung, brain, breast, kidney, skin, cervix, and ear-nose-throat cancer.

The term "thrombotic disease" particularly includes thrombo-inflammatory conditions. Thrombo-inflammation means disease states, where prothrombotic and pro-inflammatory cascades act in concert and are mechanistically linked to promote disease progression and organ damage. Thrombo-inflammatory disease states include conditions of post-ischemic organ damage, such as ischemia/reperfusion injury (I/R-injury) of the brain (in acute ischemic stroke), lung, liver, colon, myocardium, or skeletal muscle but also systemic inflammatory conditions such as sepsis or septic shock.

Preferably, the thrombotic disease is selected from the group consisting of thrombo-inflammatory conditions, venous thrombosis, arterial thrombosis, capillary thrombosis, portal vein thrombosis, renal vein thrombosis, jugular vein thrombosis, cerebral venous sinus thrombosis, thrombus formation during or after contacting blood with an artificial surface, in particular extracorporeal membrane oxygenation (ECMO), atherosclerosis, arthritis, coagulopathy, deep venous thrombosis (DVT), disseminated intravascular coagulopathy (DIC), a chronic or acute thromboembolism, pulmonary thromboembolism, Budd-Chiari syndrome, Paget-Schroetter diseases, stroke and myocardial infraction.

Determination of the effective dosage, total number of doses, and length of treatment with a soluble polypeptide of the invention is well within the capabilities of those skilled in the art, and can be determined using a standard dose escalation study. The dosage of a soluble polypeptide of the invention to be administered will vary according to the particular soluble polypeptide, the subject, and the nature and severity of the disease, the physical condition of the subject, the therapeutic regimen (e.g. whether a second therapeutic agent is used), and the selected route of administration; the appropriate dosage can be readily determined by a person skilled in the art.

The dosing schedule can vary from once a month to daily depending on a number of clinical factors, including the particular type of disease, severity of disease, and the patient's sensitivity to the soluble polypeptide of the invention. In specific embodiments, a soluble polypeptide of the invention is administered, twice weekly, every 5 days, once weekly, every 10 days, every two weeks, every three weeks, every four weeks or once a month, or in any range between any two of the foregoing values, for example from every week to every month, from every 10 days to every two weeks, or from two to three times a week, etc.

It will be recognized by one of skill in the art that the optimal quantity and spacing of individual dosages of a soluble polypeptide of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

TABLE 4

Overview of the sequences shown in the sequence listing

| SEQ ID NO: | Description |
| --- | --- |
| 1 | cDNA encoding human GPV |
| 2 | Amino acid sequence encoded by SEQ ID NO: 1; amino acids 1-16 represent the signal peptide |
| 3 | Amino acid sequence of human GPV without signal peptide |
| 4 | Amino acid sequence of soluble human GPV with poly-His tag (without signal peptide) |
| 5 | cDNA encoding murine GPV |
| 6 | Amino acid sequence encoded by SEQ ID NO: 5; amino acids 1-16 represent the signal peptide |
| 7 | Amino acid sequence of murine GPV without signal peptide |
| 8 | Amino acid sequence of soluble murine GPV with Flag-tag (without signal peptide) |
| 9 | Amino acid sequence of soluble human GPV fused to albumin via linker (without signal peptide) |
| 10 | Amino acid sequence of naturally occurring thrombin cleavage product of human GPV |

EXAMPLES

Results

Example 1: Soluble GPV has an Antithrombotic Effect

In order to investigate a potential effect of sGPV on in vivo thrombus formation in a model of mechanical injury of the abdominal aorta, 20 μg human sGPV (shGPV) were injected intravenously into WT mice directly before the experiment. Within 8 min after the aortic injury, blood flow stopped due to occlusive thrombus formation in PBS-injected control mice (FIG. 1). Pretreatment with sGPV protected WT mice from arterial occlusive thrombus formation indicating that the shGPV has an antithrombotic effect (FIG. 1).

Example 2: Soluble Human GPV Protects from Ischemic Stroke

Figure 2:
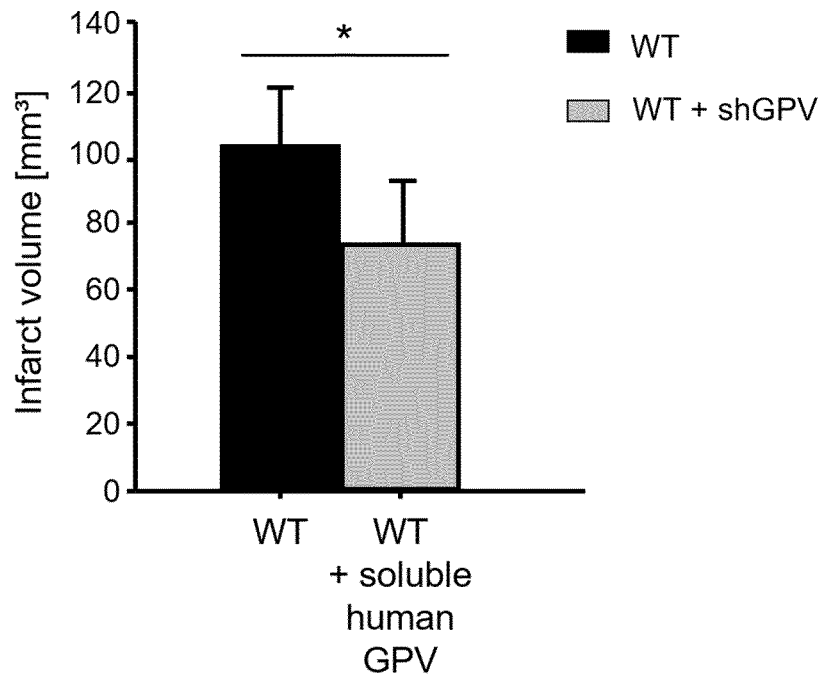
FIG. 2: Soluble human GPV protects from ischemic stroke. Mice were subjected to 60 min of transient middle cerebral artery occlusion (tMCAO). Brain infarct volumes of wildtype (black bar) and wildtype mice pretreated with shGPV-AFP (gray bar) were measured by planimetry 24 h after tMCAO. Results represent mean±SD.

To assess the role of soluble GPV in brain infarction after focal cerebral ischemia, mice were subjected to 60-minute transient middle cerebral artery occlusion (tMCAO), and infarct volume was assessed after 24 hours. Strikingly, the infarct volumes in wildtype mice treated with shGPV-AFP were significantly reduced compared with wild-type mice (FIG. 2). Thus, pre-treatment with soluble human GPV provides protection against cerebral infarct progression.

Example 3: Soluble Human GPV has No Effect on Tail Bleeding Times

Figure 3:
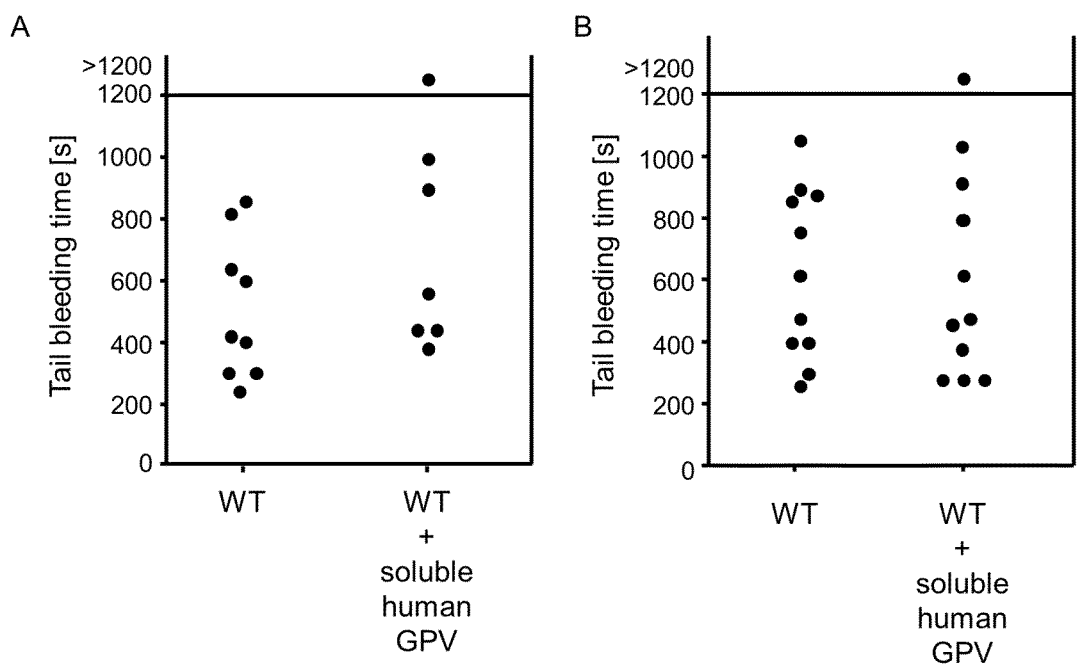
FIG. 3: Soluble GPV has no effect on tail bleeding times. Displayed are tail bleeding times of the indicated mouse lines receiving either vehicle or soluble human GPV (A: shGPV; B: shGPV-AFP). Each symbol represents one animal.
Figure 4:
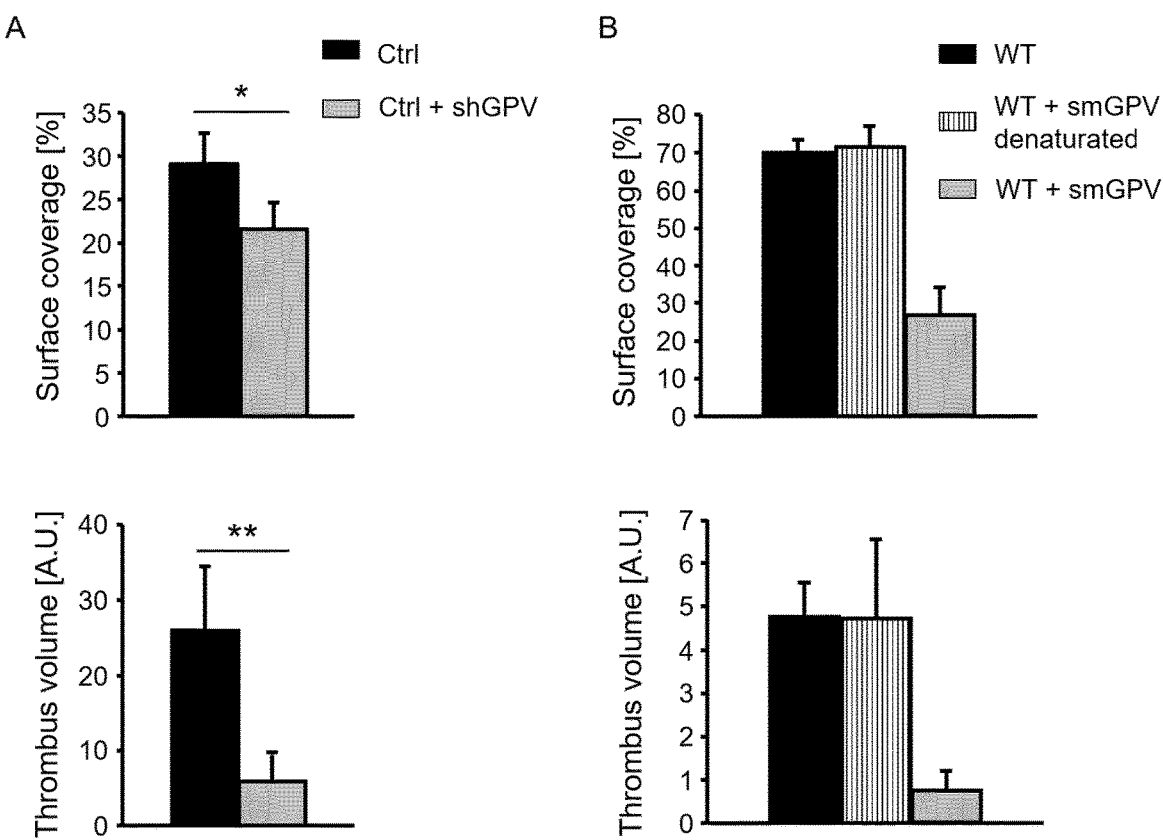
FIG. 4: Treatment with soluble GPV results in reduced surface coverage and thrombus volume on collagen under flow in vitro. A) Human blood was treated with shGPV-AFP and perfused over a collagen-coated surface at a shear rate of 1000 $s^{-1}$. B) Blood from wildtype mice was incubated with smGPV and perfused over a collagen-coated surface at a shear rate of 1700 $s^{-1}$. Results are displayed as mean±SD.

To assess the role of soluble GPV on hemostasis, mice treated either with vehicle or 20 µg soluble human GPV (shGPV) were subjected to the tail bleeding time assay. A 2-mm segment of the tail tip was removed with a scalpel. Tail bleeding was monitored by gently absorbing blood with filter paper at 20 s intervals without directly contacting the wound site. When no blood was observed on the paper, bleeding was determined to have ceased. (FIG. 3). These data demonstrate, that shGPV doses, which exert anti-thrombotic effects (FIG. 1) do not affect hemostasis indicating that shGPV is a safe anti-thrombotic agent.

Example 4: Adhesion to Collagen Under Flow In Vitro

To assess the role of soluble GPV on thrombus formation on collagen under flow in an in vitro assay, anticoagulated whole blood was incubated with 20 µg soluble GPV for 5 min and perfused over a collagen-coated surface. Human blood pretreated with shGPV-AFP (A) or wildtype blood pretreated with soluble murine GPV (B) exhibited a significantly reduced surface coverage and reduced thrombus formation. Thus, in vitro flow adhesion assay models the in vivo conditions too a large extent and reproduces the in vivo phenotype.

Materials and Methods for Examples 1-4
Mice

Animal studies were approved by the district government of Lower Franconia (Bezirksregierung Unterfranken).
Soluble GPV
1. Soluble Human GPV (shGPV)

Soluble human GPV (aa 1-518 of mature human GPV) was recombinantly expressed in baculovirus-transfected insect cells, purified using a standard nitrilotriacetic acid (Ni-NTA) column and solved in PBS buffer. Purity was checked using standard SDS PAGE.

Amino acid sequence of mature shGPV (signal peptide not shown):

(SEQ ID NO: 4)
QPFPCPPACKCVFRDAAQCSGGDVARISALGLPTNLTHILLFGMGRGVLQ

SQSFSGMTVLQRLMISDSHISAVAPGTFSDLIKLKTLRLSRNKITHLPGA

LLDKMVLLEQLFLDHNALRGIDQNMFQKLVNLQELALNQNQLDFLPASLF

TNLENLKLLDLSGNNLTHLPKGLLGAQAKLERLLLHSNRLVSLDSGLLNS

LGALTELQFHRNHIRSIAPGAFDRLPNLSSLTLSRNHLAFLPSALFLHSH

NLTLLTLFENPLAELPGVLFGEMGGLQELWLNRTQLRTLPAAAFRNLSRL

RYLGVTLSPRLSALPQGAFQGLGELQVLALHSNGLTALPDGLLRGLGKLR

QVSLRRNRLRALPRALFRNLSSLESVQLDHNQLETLPGDVFGALPRLTEV

LLGHNSWRCDCGLGPFLGWLRQHLGLVGGEEPPRCAGPGAHAGLPLWALP

GGDAECPGPRGPPPRPAADSSSEAPVHPALAPNSSEPWVWAQPVTTGKGQ

DHSPFWGFYFLLLAVQA*HHHHHHHHHH*
(Italics: poly-His tag)

2. Soluble Human GPV Fused to Albumin (shGPV-AFP)

The shGPV-AFP was expressed in CHO K1 cells and produced in a perfusion fermenter system. The cell free harvest was 30 fold concentrated using a TFF system (e.g. Centramate 500 S Pall) with a 30 kD membrane (e.g Centramate 05030T12). That concentrate was spiked with NaCl and EDTA to a final concentration of 0.75 mol/L NaCl and 5 mmol/L EDTA and loaded overnight on a Capture-Select Human Albumin column (Lifetechnologies) which was preequlibrated with 20 mM Tris buffer pH 7.4. After washing the column with equilibration buffer shGPV-AFP was eluted with 20 mM Tris plus 2 M MgCl pH 7.4 buffer. The eluate was than concentrated and dialyzed against 50 mM Tris+150 mM NaCl pH7.4 using Ultra Centrifugal Filters with a 30 kD cut off (e.g. Amicon Ref. UFC903024).

Amino acid sequence of mature shGPV-AFP (signal peptide not shown):

(SEQ ID NO: 9)
QPFPCPPACKCVFRDAAQCSGGDVARISALGLPTNLTHILLFGMGRGVLQ

SQSFSGMTVLQRLMISDSHISAVAPGTFSDLIKLKTLRLSRNKITHLPGA

LLDKMVLLEQLFLDHNALRGIDQNMFQKLVNLQELALNQNQLDFLPASLF

TNLENLKLLDLSGNNLTHLPKGLLGAQAKLERLLLHSNRLVSLDSGLLNS

LGALTELQFHRNHIRSIAPGAFDRLPNLSSLTLSRNHLAFLPSALFLHSH

NLTLLTLFENPLAELPGVLFGEMGGLQELWLNRTQLRTLPAAAFRNLSRL

RYLGVTLSPRLSALPQGAFQGLGELQVLALHSNGLTALPDGLLRGLGKLR

QVSLRRNRLRALPRALFRNLSSLESVQLDHNQLETLPGDVFGALPRLTEV

LLGHNSWRCDCGLGPFLGWLRQHLGLVGGEEPPRCAGPGAHAGLPLWALP

GGDAECPG*PRAVGSGGSGGSGGSGGSGGSGGSGGSGGSGGSGS*DAHKSEV

*AHRFKDLGEENFKALVLIAFAQYLQQCPFEDHVKLVNEVTEFAKTCVA*

*DESAENCDKSLHTLFGDKLCTVATLRETYGEMADCCAKQEPERNECFL*

*QHKDDNPNLPRLVRPEVDVMCTAFHDNEETFLKKYLYEIARRHPYFYA*

*PELLFFAKRYKAAFTECCQAADKAACLLPKLDELRDEGKASSAKQRLK*

*CASLQKFGERAFKAWAVARLSQRFPKAEFAEVSKLVTDLTKVHTECCH*

*GDLLECADDRADLAKYICENQDSISSKLKECCEKPLLEKSHCIAEVEN*

*DEMPADLPSLAADFVESKDVCKNYAEAKDVFLGMFLYEYARRHPDYSV*

*VLLLRLAKTYETTLEKCCAAADPHECYAKVFDEFKPLVEEPQNLIKQN*

*CELFEQLGEYKFQNALLVRYTKKVPQVSTPTLVEVSRNLGKVGSKCCK*

*HPEAKRMPCAEDYLSVVLNQLCVLHEKTPVSDRVTKCCTESLVNRRPC*

*FSALEVDETYVPKEFNAETFTFHADICTLSEKERQIKKQTALVELVKH*

-continued

KPKATKEQLKAVMDDFAAFVEKCCKADDKETCFAEEGKKLVAASQAAL

GL (Underlined: thrombin cleavage site and GGS Linker; Italics: human albumin sequence)

3. Soluble Murine GPV (smGPV)

Soluble murine GPV (aa 1-519 of mature murine GPV) was recombinantly expressed in CHO cells, purified using an anti-Flag column and solved in PBS buffer. Purity was checked using standard SDS PAGE.

Amino acid sequence of mature smGPV (signal peptide not shown):

(SEQ ID NO: 8)
QPFPCPKTCKCVVRDAAQCSGGSVAHIAELGLPTNLTHILLFRMDQGILR

NHSFSGMTVLQRQMLSDSHISAIDPGTFNDLVKLKTLRLTRNKISRLPRA

ILDKMVLLEQLFLDHNALRDLDQNLFQQLRNLQELGLNQNQLSFLPANLF

SSLRELKLLDLSRNNLTHLPKGLLGAQVKLEKLLLYSNQLTSVDSGLLSN

LGALTELRLERNHLRSVAPGAFDRLGNLSSLTLSGNLLESLPPALFLHVS

SVSRLTLFENPLEELPDVLFGEMAGLRELWLNGTHLSTLPAAAFRNLSGL

QTLGLTRNPRLSALPRGVFQGLRELRVLGLHTNALAELRDDALRGLGHLR

QVSLRHNRLRALPRTLFRNLSSLESVQLEHNQLETLPGDVFAALPQLTQV

LLGHNPWLCDCGLWRFLQWLRHHPDILGRDEPPQCRGPEPRASLSFWELL

QGDPWCPDPRSLPLDPPTENALEAPVPSWLPNSWQSQTWAQLVARGESPN

NRLECGRNPAFLYKVVLEM*DYKDDDDK*
(Italics: Flag tag)

Mechanical-Injury of the Abdominal Aorta

To open the abdominal cavity of anesthetized mice (10-16 weeks of age), a longitudinal midline incision was performed and the abdominal aorta was exposed. A Doppler ultrasonic flow probe (Transonic Systems, Maastricht, Netherlands) was placed around the aorta and thrombosis was induced by a mechanical injury with a single firm compression (15 s) of a forceps upstream of the flow probe. Blood flow was monitored until complete occlusion occurred or 30 min had elapsed.

Transient Middle Cerebral Artery Occlusion (tMCAO)

Focal cerebral ischemia was induced in 8-to-12-week-old mice by a transient middle cerebral artery occlusion (tMCAO). Inhalation anesthesia was induced by 2% isoflurane in a 70% $N_2$/30% $O_2$ mixture and a servo-controlled heating device was used to record and maintain body temperature during the surgical procedure. The duration of the surgical procedure per animals was kept below 15 minutes. A silicon rubber-coated 6.0 nylon monofilament (6021PK10, Doccol, Redlands, Calif., USA) was advanced through the carotid artery up to the origin of the middle cerebral artery (MCA) causing an MCA infarction. After an occlusion time of 60 min, the filament was removed allowing reperfusion. Animals were sacrificed 24 h after reperfusion and brains were checked for intracerebral hemorrhages. The extent of infarction was quantitatively assessed 24 hours after reperfusion on 2,3,5-triphenyltetrazolium chloride (TTC, Sigma-Aldrich) (2% (w/v) solution) stained brain sections. Planimetric measurements of infarcted areas (ImageJ software, NIH, Bethesda, Md., USA) corrected for brain edema were performed in a blinded fashion.

Bleeding Time Assay

Mice were anesthetized by intraperitoneal injection of triple anesthesia and a 2-mm segment of the tail tip was removed with a scalpel. Tail bleeding was monitored by gently absorbing blood with filter paper at 20 s intervals without directly contacting the wound site. When no blood was observed on the paper, bleeding was determined to have ceased. The experiment was manually stopped after 20 min by cauterization.

Thrombus Formation on Collagen Under Flow In Vitro

For adhesion to collagen, coverslips were coated with 200 µg mL$^{-1}$ collagen I at 37° C. o/n and blocked for 1 h with 1% BSA in PBS. Whole blood (700 µl+300 µl heparin (20 U/ml in TBS, pH7.3)) was diluted 2:1 in Tyrode's buffer containing $Ca^{2+}$ and filled into a 1 ml syringe. Before perfusion, anticoagulated blood was incubated with Dylight-488-conjugated anti-GPIX derivative (0.2 µg/mL) at 37° C. for 5 minutes. Transparent flow chambers with a slit depth of 50 µm, equipped with the coated coverslips, were connected to a syringe that was filled with diluted whole blood. Perfusion was performed using a pulse-free pump under high shear stress equivalent to a wall shear rate of 1000 s$^{-1}$ or 1,700 s$^{-1}$. Aggregate formation was visualized with a Zeiss Axiovert 200 inverted microscope (40 x/0.60 objective). Phase-contrast and fluorescence pictures were recorded with a CoolSNAP-EZ camera, and analyzed off-line using MetaVue software.

Statistical Analysis

Results are shown as mean±SD from at least three individual experiments per group. When applicable Fisher's exact test was used for statistical analysis. Otherwise, the Welch's t test was performed for statistical analysis. P-values <0.05 were considered statistically significant.

The invention claimed is:

1. A method for the treatment and/or prevention of a thrombotic disease in a subject, comprising administering to the subject an effective amount of a soluble polypeptide comprising a modified glycoprotein V (GPV) lacking a functional transmembrane domain,
   wherein the modified GPV comprises an amino acid sequence at least 75% identical to amino acids 1-503 of SEQ ID NO:3 or amino acids 1-502 of SEQ ID NO:7, and
   wherein the thrombotic disease is selected from the group consisting of thrombo-inflammatory conditions, venous thrombosis, arterial thrombosis, capillary thrombosis, portal vein thrombosis, renal vein thrombosis, jugular vein thrombosis, cerebral venous sinus thrombosis, thrombus formation during or after contacting blood with an artificial surface, atherosclerosis, arthritis, coagulopathy, deep venous thrombosis (DVT), disseminated intravascular coagulopathy (DIC), a chronic or acute thromboembolism, pulmonary thromboembolism, Budd-Chiari syndrome, Paget-Schroetter diseases, stroke, and myocardial infarction.

2. The method according to claim 1, wherein the modified GPV is a truncated GPV.

3. The method according to claim 1, wherein the modified GPV consists of a fragment of the extracellular domain of a native GPV.

4. The method according to claim 3, wherein the native GPV consists of the amino acid sequence of SEQ ID NO:3.

5. The method according to claim 1, wherein the soluble polypeptide is a non-naturally occurring polypeptide.

6. The method according to claim 5, wherein the soluble peptide further comprises a half-life-extending moiety.

7. The method according to claim 6, wherein the half-life-extending moiety is conjugated to the modified GPV.

8. The method according to claim 7, wherein the half-life-extending moiety is selected from the group consisting of hydroxyethyl starch (HES), polyethylene glycol (PEG), polysialic acids (PSAs), and albumin binding ligands.

9. The method according to claim 6, wherein the half-life-extending moiety is a heterologous amino acid sequence fused to the modified GPV, either directly or via a linker.

10. The method according to claim 9, wherein the heterologous amino acid sequence comprises or consists of a polypeptide selected from the group consisting of albumin and a fragment thereof having a length of at least 100 amino acids, immunoglobulin constant regions and fragments thereof, transferrin and fragments thereof, the C-terminal peptide of human chorionic gonadotropin, solvated random chains with large hydrodynamic volume (XTEN), homo-amino acid repeats (HAP), proline-alanine-serine repeats (PAS), afamin, alpha-fetoprotein, Vitamin D binding protein, polypeptides capable of binding under physiological conditions to albumin or immunoglobulin constant regions, and combinations thereof.

11. The method according to claim 1, wherein the soluble polypeptide is obtained by recombinant expression in mammalian cells.

12. The method according to claim 1, further comprising administering to the subject an anti-platelet or an anti-coagulant drug.

13. The method of claim 1, wherein the thrombotic disease is thrombus formation during or after extracorporeal membrane oxygenation (ECMO).

14. The method of claim 7, wherein the half-life-extending moiety is a fatty acid chain.

15. The method of claim 9, wherein the heterologous amino acid sequence comprises an Fc fragment.

16. The method of claim 1, wherein the modified GPV comprises amino acids 1-503 of SEQ ID NO:3 or amino acids 1-502 of SEQ ID NO:7.

17. The method of claim 1, wherein the modified GPV comprises amino acids 1-518 of SEQ ID NO:3 or amino acids 1-519 of SEQ ID NO:7.

18. The method of claim 1, wherein the modified GPV comprises amino acids 1-516 of SEQ ID NO:3.

19. The method of claim 1, wherein the modified GPV lacks the transmembrane domain of a native GPV.

* * * * *

SEQUENCE LISTING

```
<160> NUMBER OF SEQ ID NOS: 10

<210> SEQ ID NO 1
<211> LENGTH: 3493
<212> TYPE: DNA
<213> ORGANISM: Homo sapiens
<220> FEATURE:
<221> NAME/KEY: CDS
<222> LOCATION: (32)..(1714)

<400> SEQUENCE: 1
agttactttg gagtgcagaa ccatttcaga c atg ctg agg ggg act cta ctg       52
                                   Met Leu Arg Gly Thr Leu Leu
                                   1               5
```

-continued

| | | |
|---|---|---|
| tgc gcg gtg ctc ggg ctt ctg cgc gcc cag ccc ttc ccc tgt ccg cca<br>Cys Ala Val Leu Gly Leu Leu Arg Ala Gln Pro Phe Pro Cys Pro Pro<br>          10                      15                          20 | 100 |
| gct tgc aag tgt gtc ttc cgg gac gcc gcg cag tgc tcg ggg ggc gac<br>Ala Cys Lys Cys Val Phe Arg Asp Ala Ala Gln Cys Ser Gly Gly Asp<br>     25                      30                      35 | 148 |
| gtg gcg cgc atc tcc gcg cta ggc ctg ccc acc aac ctc acg cac atc<br>Val Ala Arg Ile Ser Ala Leu Gly Leu Pro Thr Asn Leu Thr His Ile<br>40                     45                      50                      55 | 196 |
| ctg ctc ttc gga atg ggc cgc ggc gtc ctg cag agc cag agc ttc agc<br>Leu Leu Phe Gly Met Gly Arg Gly Val Leu Gln Ser Gln Ser Phe Ser<br>             60                      65                      70 | 244 |
| ggc atg acc gtc ctg cag cgc ctc atg atc tcc gac agc cac att tcc<br>Gly Met Thr Val Leu Gln Arg Leu Met Ile Ser Asp Ser His Ile Ser<br>        75                      80                      85 | 292 |
| gcc gtt gcc ccc ggc acc ttc agt gac ctg ata aaa ctg aaa acc ctg<br>Ala Val Ala Pro Gly Thr Phe Ser Asp Leu Ile Lys Leu Lys Thr Leu<br>           90                      95                      100 | 340 |
| agg ctg tcg cgc aac aaa atc acg cat ctt cca ggt gcg ctg ctg gat<br>Arg Leu Ser Arg Asn Lys Ile Thr His Leu Pro Gly Ala Leu Leu Asp<br>     105                      110                      115 | 388 |
| aag atg gtg ctc ctg gag cag ttg ttt ttg gac cac aat gcg cta agg<br>Lys Met Val Leu Leu Glu Gln Leu Phe Leu Asp His Asn Ala Leu Arg<br>120                    125                      130                      135 | 436 |
| ggc att gac caa aac atg ttt cag aaa ctg gtt aac ctg cag gag ctc<br>Gly Ile Asp Gln Asn Met Phe Gln Lys Leu Val Asn Leu Gln Glu Leu<br>                140                      145                      150 | 484 |
| gct ctg aac cag aat cag ctc gat ttc ctt cct gcc agt ctc ttc acg<br>Ala Leu Asn Gln Asn Gln Leu Asp Phe Leu Pro Ala Ser Leu Phe Thr<br>                     155                      160                      165 | 532 |
| aat ctg gag aac ctg aag ttg ttg gat tta tcg gga aac aac ctg acc<br>Asn Leu Glu Asn Leu Lys Leu Leu Asp Leu Ser Gly Asn Asn Leu Thr<br>           170                      175                      180 | 580 |
| cac ctg ccc aag ggg ttg ctt gga gca cag gct aag ctc gag aga ctt<br>His Leu Pro Lys Gly Leu Leu Gly Ala Gln Ala Lys Leu Glu Arg Leu<br>185                    190                      195 | 628 |
| ctg ctc cac tcg aac cgc ctt gtg tct ctg gat tcg ggg ctg ttg aac<br>Leu Leu His Ser Asn Arg Leu Val Ser Leu Asp Ser Gly Leu Leu Asn<br>200                    205                      210                      215 | 676 |
| agc ctg ggc gcc ctg acg gag ctg cag ttc cac cga aat cac atc cgt<br>Ser Leu Gly Ala Leu Thr Glu Leu Gln Phe His Arg Asn His Ile Arg<br>                   220                      225                      230 | 724 |
| tcc atc gca ccc ggg gcc ttc gac cgg ctc cca aac ctc agt tct ttg<br>Ser Ile Ala Pro Gly Ala Phe Asp Arg Leu Pro Asn Leu Ser Ser Leu<br>                   235                      240                      245 | 772 |
| acg ctt tcg aga aac cac ctt gcg ttt ctc ccc tct gcg ctc ttt ctt<br>Thr Leu Ser Arg Asn His Leu Ala Phe Leu Pro Ser Ala Leu Phe Leu<br>           250                      255                      260 | 820 |
| cat tcg cac aat ctg act ctg ttg act ctg ttc gag aac ccg ctg gca<br>His Ser His Asn Leu Thr Leu Leu Thr Leu Phe Glu Asn Pro Leu Ala<br>265                    270                      275 | 868 |
| gag ctc ccg ggg gtg ctc ttc ggg gag atg ggg ggc ctg cag gag ctg<br>Glu Leu Pro Gly Val Leu Phe Gly Glu Met Gly Gly Leu Gln Glu Leu<br>280                    285                      290                      295 | 916 |
| tgg ctg aac cgc acc cag ctg cgc acc ctg ccc gcc gcc gcc ttc cgc<br>Trp Leu Asn Arg Thr Gln Leu Arg Thr Leu Pro Ala Ala Ala Phe Arg<br>                   300                      305                      310 | 964 |
| aac ctg agc cgc ctg cgg tac tta ggg gtg act ctg agc ccg cgg ctg<br>Asn Leu Ser Arg Leu Arg Tyr Leu Gly Val Thr Leu Ser Pro Arg Leu | 1012 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 315 |     |     |     | 320 |     |     |     |     | 325 |     |     |     |     |      |
| agc | gcg | ctt | ccg | cag | ggc | gcc | ttc | cag | ggc | ctt | ggc | gag | ctc | cag | gtg | 1060 |
| Ser | Ala | Leu | Pro | Gln | Gly | Ala | Phe | Gln | Gly | Leu | Gly | Glu | Leu | Gln | Val |      |
|     |     | 330 |     |     |     | 335 |     |     |     |     | 340 |     |     |     |     |      |
| ctc | gcc | ctg | cac | tcc | aac | ggc | ctg | acc | gcc | ctc | ccc | gac | ggc | ttg | ctg | 1108 |
| Leu | Ala | Leu | His | Ser | Asn | Gly | Leu | Thr | Ala | Leu | Pro | Asp | Gly | Leu | Leu |      |
|     |     | 345 |     |     |     | 350 |     |     |     |     | 355 |     |     |     |     |      |
| cgc | ggc | ctc | ggc | aag | ctg | cgc | cag | gtg | tcc | ctg | cgc | cgc | aac | agg | ctg | 1156 |
| Arg | Gly | Leu | Gly | Lys | Leu | Arg | Gln | Val | Ser | Leu | Arg | Arg | Asn | Arg | Leu |      |
| 360 |     |     |     |     | 365 |     |     |     |     | 370 |     |     |     |     | 375 |      |
| cgc | gcc | ctg | ccc | cgt | gcc | ctc | ttc | cgc | aat | ctc | agc | agc | ctg | gag | agc | 1204 |
| Arg | Ala | Leu | Pro | Arg | Ala | Leu | Phe | Arg | Asn | Leu | Ser | Ser | Leu | Glu | Ser |      |
|     |     |     |     | 380 |     |     |     |     | 385 |     |     |     |     | 390 |     |      |
| gtc | cag | ctc | gac | cac | aac | cag | ctg | gag | acc | ctg | cct | ggc | gac | gtg | ttt | 1252 |
| Val | Gln | Leu | Asp | His | Asn | Gln | Leu | Glu | Thr | Leu | Pro | Gly | Asp | Val | Phe |      |
|     |     |     |     | 395 |     |     |     |     | 400 |     |     |     |     | 405 |     |      |
| ggg | gct | ctg | ccc | cgg | ctg | acg | gag | gtc | ctg | ttg | ggg | cac | aac | tcc | tgg | 1300 |
| Gly | Ala | Leu | Pro | Arg | Leu | Thr | Glu | Val | Leu | Leu | Gly | His | Asn | Ser | Trp |      |
|     |     | 410 |     |     |     | 415 |     |     |     |     | 420 |     |     |     |     |      |
| cgc | tgc | gac | tgt | ggc | ctg | ggg | ccc | ttc | ctg | ggg | tgg | ctg | cgg | cag | cac | 1348 |
| Arg | Cys | Asp | Cys | Gly | Leu | Gly | Pro | Phe | Leu | Gly | Trp | Leu | Arg | Gln | His |      |
|     |     | 425 |     |     |     | 430 |     |     |     |     | 435 |     |     |     |     |      |
| cta | ggc | ctc | gtg | ggc | ggg | gaa | gag | ccc | cca | cgg | tgc | gca | ggc | cct | ggg | 1396 |
| Leu | Gly | Leu | Val | Gly | Gly | Glu | Glu | Pro | Pro | Arg | Cys | Ala | Gly | Pro | Gly |      |
| 440 |     |     |     |     | 445 |     |     |     |     | 450 |     |     |     |     | 455 |      |
| gcg | cac | gcc | ggc | ctg | ccg | ctc | tgg | gcc | ctg | ccg | ggg | ggt | gac | gcg | gag | 1444 |
| Ala | His | Ala | Gly | Leu | Pro | Leu | Trp | Ala | Leu | Pro | Gly | Gly | Asp | Ala | Glu |      |
|     |     |     |     | 460 |     |     |     |     | 465 |     |     |     |     | 470 |     |      |
| tgc | ccg | ggc | ccc | cgg | ggc | ccg | cct | ccc | cgc | ccc | gct | gcg | gac | agc | tcc | 1492 |
| Cys | Pro | Gly | Pro | Arg | Gly | Pro | Pro | Pro | Arg | Pro | Ala | Ala | Asp | Ser | Ser |      |
|     |     |     |     | 475 |     |     |     |     | 480 |     |     |     |     | 485 |     |      |
| tcg | gaa | gcc | cct | gtc | cac | cca | gcc | ttg | gct | ccc | aac | agc | tca | gaa | ccc | 1540 |
| Ser | Glu | Ala | Pro | Val | His | Pro | Ala | Leu | Ala | Pro | Asn | Ser | Ser | Glu | Pro |      |
|     |     |     |     | 490 |     |     |     |     | 495 |     |     |     |     | 500 |     |      |
| tgg | gtg | tgg | gcc | cag | ccg | gtg | acc | acg | ggc | aaa | ggt | caa | gat | cat | agt | 1588 |
| Trp | Val | Trp | Ala | Gln | Pro | Val | Thr | Thr | Gly | Lys | Gly | Gln | Asp | His | Ser |      |
|     |     | 505 |     |     |     | 510 |     |     |     |     | 515 |     |     |     |     |      |
| ccg | ttc | tgg | ggg | ttt | tat | ttt | ctg | ctt | tta | gct | gtt | cag | gcc | atg | atc | 1636 |
| Pro | Phe | Trp | Gly | Phe | Tyr | Phe | Leu | Leu | Leu | Ala | Val | Gln | Ala | Met | Ile |      |
| 520 |     |     |     |     | 525 |     |     |     |     | 530 |     |     |     |     | 535 |      |
| acc | gtg | atc | atc | gtg | ttt | gct | atg | att | aaa | att | ggc | caa | ctc | ttt | cga | 1684 |
| Thr | Val | Ile | Ile | Val | Phe | Ala | Met | Ile | Lys | Ile | Gly | Gln | Leu | Phe | Arg |      |
|     |     |     |     | 540 |     |     |     |     | 545 |     |     |     |     | 550 |     |      |
| aaa | tta | atc | aga | gag | aga | gcc | ctt | ggg | taa | accaatggga | | | | aaatcttcta | | 1734 |
| Lys | Leu | Ile | Arg | Glu | Arg | Ala | Leu | Gly |     |     |     |     |     |     |     |      |
|     |     |     |     | 555 |     |     |     |     | 560 |     |     |     |     |     |     |      |

| | | |
|---|---|---|
| attacttaga acctgaccag atgtggctcg gaggggaatc cagacccgct gctgtcttgc | | 1794 |
| tctccctccc ctccccactc ctcctctctt cttcctcttc tctctcactg ccacgccttc | | 1854 |
| ctttccctcc tcctccccct ctccgctctg tgctcttcat tctcacaggc ccgcaacccc | | 1914 |
| tcctctctgt gtccccgcc cgttcctgga aactgagctt gacgtttgta aactgtggtt | | 1974 |
| gcctgccttc cccagctccc acgcgggtgt gcgctgacac tgccggggc gctggactgt | | 2034 |
| gttggaccca tccgtgctcc gctgtgcctg gcttggcgtc tggtggagag aggggcctct | | 2094 |
| tcagtgtcta ctgagtaagg ggacagctcc aggccgggc ctgtctcctg cacagagtaa | | 2154 |
| gccggtaaat gtttgtgaaa tcaatgcgtg gataaaggaa cacatgccat ccaagtgatg | | 2214 |
| atggcttttc ctggagggaa aggataggct gttgctctat ctaatttttt gttttgtttt | | 2274 |

```
ttggacagtc tagctctgtg gcccaggctg gcgtgcagtg ggccgtctca gttcactgca   2334
gcctccgcct cccaggttca agtgattctc atgcctcagc gttctgagta gctgggatta   2394
gaggcgtgtg ccactacacc cggctaattt ttgtactttt taaagtagag acggggcttt   2454
gccatattgg cctggctgat ctcaaactcc tggtcttgaa ctcctggcca caagtgatct   2514
gcccgccttg gcctcccaaa gtgctgggat tacaggcgta agccactaca cctggccctc   2574
ttcatcgaat tttatttgag aagtagagct cttgccattt tttcccttgc tccattttc    2634
tcactttatg tctctctgac ctatgggcta cttgggagag cactggactc cattcatgca   2694
tgagcatttt caggataagc gacttctgtg aggctgagag aggaagaaaa cacggagcct   2754
tccctccagg tgcccagtgt aggtccagcg tgtttcctga gcctcctgtg agtttccact   2814
tgctttacat ccatgcaaca tgtcattttg aaactggatt gatttgcatt tcctggaact   2874
ctgccacctc atttcacaag catttatgga gcagttaaca tgtgactggt attcatgaat   2934
ataatgataa gcttgattct agttcagctg ctgtcacagt ctcatttgtt cttccaactg   2994
aaagccgtaa aacctttgtt gctttaattg aatgtctgtg cttatgagag gcagtggtta   3054
aaacaggggc tggcgagttg acaactgtgg gttcaaatcc cagctctacc acttactaac   3114
tgcatgggac tttgggtaag acacctgctt acattctcta agccttggtt tcctgaacct   3174
taaaacagga taacatagta cctgcttcgt agagttttg tgagaattaa aggcaataaa    3234
gcatataatg acttagccca gcggcctgca ggcaatacat gttaatgaat gttagctatt   3294
attactaaag gatgagcaat tattattggc atcatgattt ctaaagaaga gctttgagtt   3354
ggtatttttc tctgtgtata agggtaagtc cgaactttct cagactggag gttacattca   3414
catcagtctg tcttcccctg cggatggcct cagccctggg tggccagact ctgtgctcac   3474
aatccagagc aatggatcc                                                 3493
```

<210> SEQ ID NO 2
<211> LENGTH: 560
<212> TYPE: PRT
<213> ORGANISM: Homo sapiens

<400> SEQUENCE: 2

Met Leu Arg Gly Thr Leu Leu Cys Ala Val Leu Gly Leu Leu Arg Ala
1               5                   10                  15

Gln Pro Phe Pro Cys Pro Ala Cys Lys Cys Val Phe Arg Asp Ala
            20                  25                  30

Ala Gln Cys Ser Gly Gly Asp Val Ala Arg Ile Ser Ala Leu Gly Leu
        35                  40                  45

Pro Thr Asn Leu Thr His Ile Leu Leu Phe Gly Met Gly Arg Gly Val
    50                  55                  60

Leu Gln Ser Gln Ser Phe Ser Gly Met Thr Val Leu Gln Arg Leu Met
65                  70                  75                  80

Ile Ser Asp Ser His Ile Ser Ala Val Ala Pro Gly Thr Phe Ser Asp
                85                  90                  95

Leu Ile Lys Leu Lys Thr Leu Arg Leu Ser Arg Asn Lys Ile Thr His
            100                 105                 110

Leu Pro Gly Ala Leu Leu Asp Lys Met Val Leu Glu Gln Leu Phe
        115                 120                 125

Leu Asp His Asn Ala Leu Arg Gly Ile Asp Gln Asn Met Phe Gln Lys
    130                 135                 140

Leu Val Asn Leu Gln Glu Leu Ala Leu Asn Gln Asn Gln Leu Asp Phe

```
            145                 150                 155                 160
Leu Pro Ala Ser Leu Phe Thr Asn Leu Glu Asn Leu Lys Leu Leu Asp
                165                 170                 175
Leu Ser Gly Asn Asn Leu Thr His Leu Pro Lys Gly Leu Leu Gly Ala
                180                 185                 190
Gln Ala Lys Leu Glu Arg Leu Leu His Ser Asn Arg Leu Val Ser
                195                 200                 205
Leu Asp Ser Gly Leu Leu Asn Ser Leu Gly Ala Leu Thr Glu Leu Gln
210                 215                 220
Phe His Arg Asn His Ile Arg Ser Ile Ala Pro Gly Ala Phe Asp Arg
225                 230                 235                 240
Leu Pro Asn Leu Ser Ser Leu Thr Leu Ser Arg Asn His Leu Ala Phe
                245                 250                 255
Leu Pro Ser Ala Leu Phe Leu His Ser His Asn Leu Thr Leu Leu Thr
                260                 265                 270
Leu Phe Glu Asn Pro Leu Ala Glu Leu Pro Gly Val Leu Phe Gly Glu
                275                 280                 285
Met Gly Gly Leu Gln Glu Leu Trp Leu Asn Arg Thr Gln Leu Arg Thr
290                 295                 300
Leu Pro Ala Ala Ala Phe Arg Asn Leu Ser Arg Leu Arg Tyr Leu Gly
305                 310                 315                 320
Val Thr Leu Ser Pro Arg Leu Ser Ala Leu Pro Gln Gly Ala Phe Gln
                325                 330                 335
Gly Leu Gly Glu Leu Gln Val Leu Ala Leu His Ser Asn Gly Leu Thr
                340                 345                 350
Ala Leu Pro Asp Gly Leu Leu Arg Gly Leu Gly Lys Leu Arg Gln Val
                355                 360                 365
Ser Leu Arg Arg Asn Arg Leu Arg Ala Leu Pro Arg Ala Leu Phe Arg
                370                 375                 380
Asn Leu Ser Ser Leu Glu Ser Val Gln Leu Asp His Asn Gln Leu Glu
385                 390                 395                 400
Thr Leu Pro Gly Asp Val Phe Gly Ala Leu Pro Arg Leu Thr Glu Val
                405                 410                 415
Leu Leu Gly His Asn Ser Trp Arg Cys Asp Cys Gly Leu Gly Pro Phe
                420                 425                 430
Leu Gly Trp Leu Arg Gln His Leu Gly Leu Val Gly Gly Glu Glu Pro
                435                 440                 445
Pro Arg Cys Ala Gly Pro Gly Ala His Ala Gly Leu Pro Leu Trp Ala
                450                 455                 460
Leu Pro Gly Gly Asp Ala Glu Cys Pro Gly Pro Arg Gly Pro Pro Pro
465                 470                 475                 480
Arg Pro Ala Ala Asp Ser Ser Ser Glu Ala Pro Val His Pro Ala Leu
                485                 490                 495
Ala Pro Asn Ser Ser Glu Pro Trp Val Trp Ala Gln Pro Val Thr Thr
                500                 505                 510
Gly Lys Gly Gln Asp His Ser Pro Phe Trp Gly Phe Tyr Phe Leu Leu
                515                 520                 525
Leu Ala Val Gln Ala Met Ile Thr Val Ile Ile Val Phe Ala Met Ile
                530                 535                 540
Lys Ile Gly Gln Leu Phe Arg Lys Leu Ile Arg Glu Arg Ala Leu Gly
545                 550                 555                 560
```

<210> SEQ ID NO 3

<211> LENGTH: 544
<212> TYPE: PRT
<213> ORGANISM: Homo sapiens

<400> SEQUENCE: 3

```
Gln Pro Phe Pro Cys Pro Pro Ala Cys Lys Cys Val Phe Arg Asp Ala
1               5                   10                  15

Ala Gln Cys Ser Gly Gly Asp Val Ala Arg Ile Ser Ala Leu Gly Leu
            20                  25                  30

Pro Thr Asn Leu Thr His Ile Leu Leu Phe Gly Met Gly Arg Gly Val
        35                  40                  45

Leu Gln Ser Gln Ser Phe Ser Gly Met Thr Val Leu Gln Arg Leu Met
    50                  55                  60

Ile Ser Asp Ser His Ile Ser Ala Val Ala Pro Gly Thr Phe Ser Asp
65                  70                  75                  80

Leu Ile Lys Leu Lys Thr Leu Arg Leu Ser Arg Asn Lys Ile Thr His
                85                  90                  95

Leu Pro Gly Ala Leu Leu Asp Lys Met Val Leu Leu Glu Gln Leu Phe
            100                 105                 110

Leu Asp His Asn Ala Leu Arg Gly Ile Asp Gln Asn Met Phe Gln Lys
        115                 120                 125

Leu Val Asn Leu Gln Glu Leu Ala Leu Asn Gln Asn Gln Leu Asp Phe
    130                 135                 140

Leu Pro Ala Ser Leu Phe Thr Asn Leu Glu Asn Leu Lys Leu Leu Asp
145                 150                 155                 160

Leu Ser Gly Asn Asn Leu Thr His Leu Pro Lys Gly Leu Leu Gly Ala
                165                 170                 175

Gln Ala Lys Leu Glu Arg Leu Leu His Ser Asn Arg Leu Val Ser
            180                 185                 190

Leu Asp Ser Gly Leu Leu Asn Ser Leu Gly Ala Leu Thr Glu Leu Gln
        195                 200                 205

Phe His Arg Asn His Ile Arg Ser Ile Ala Pro Gly Ala Phe Asp Arg
    210                 215                 220

Leu Pro Asn Leu Ser Ser Leu Thr Leu Ser Arg Asn His Leu Ala Phe
225                 230                 235                 240

Leu Pro Ser Ala Leu Phe Leu His Ser His Asn Leu Thr Leu Thr
                245                 250                 255

Leu Phe Glu Asn Pro Leu Ala Glu Leu Pro Gly Val Leu Phe Gly Glu
            260                 265                 270

Met Gly Gly Leu Gln Glu Leu Trp Leu Asn Arg Thr Gln Leu Arg Thr
        275                 280                 285

Leu Pro Ala Ala Ala Phe Arg Asn Leu Ser Arg Leu Arg Tyr Leu Gly
    290                 295                 300

Val Thr Leu Ser Pro Arg Leu Ser Ala Leu Pro Gln Gly Ala Phe Gln
305                 310                 315                 320

Gly Leu Gly Glu Leu Gln Val Leu Ala Leu His Ser Asn Gly Leu Thr
                325                 330                 335

Ala Leu Pro Asp Gly Leu Leu Arg Gly Leu Gly Lys Leu Arg Gln Val
            340                 345                 350

Ser Leu Arg Arg Asn Arg Leu Arg Ala Leu Pro Arg Ala Leu Phe Arg
        355                 360                 365

Asn Leu Ser Ser Leu Glu Ser Val Gln Leu Asp His Asn Gln Leu Glu
    370                 375                 380

Thr Leu Pro Gly Asp Val Phe Gly Ala Leu Pro Arg Leu Thr Glu Val
```

```
               385                 390                 395                 400
Leu Leu Gly His Asn Ser Trp Arg Cys Asp Cys Gly Leu Gly Pro Phe
                405                 410                 415
Leu Gly Trp Leu Arg Gln His Leu Gly Leu Val Gly Gly Glu Glu Pro
            420                 425                 430
Pro Arg Cys Ala Gly Pro Ala His Ala Gly Leu Pro Leu Trp Ala
        435                 440                 445
Leu Pro Gly Gly Asp Ala Glu Cys Pro Gly Pro Arg Gly Pro Pro Pro
450                 455                 460
Arg Pro Ala Ala Asp Ser Ser Glu Ala Pro Val His Pro Ala Leu
465                 470                 475                 480
Ala Pro Asn Ser Ser Glu Pro Trp Val Trp Ala Gln Pro Val Thr Thr
                485                 490                 495
Gly Lys Gly Gln Asp His Ser Pro Phe Trp Gly Phe Tyr Phe Leu Leu
                500                 505                 510
Leu Ala Val Gln Ala Met Ile Thr Val Ile Ile Val Phe Ala Met Ile
            515                 520                 525
Lys Ile Gly Gln Leu Phe Arg Lys Leu Ile Arg Glu Arg Ala Leu Gly
        530                 535                 540

<210> SEQ ID NO 4
<211> LENGTH: 527
<212> TYPE: PRT
<213> ORGANISM: Artificial Sequence
<220> FEATURE:
<223> OTHER INFORMATION: Soluble GPV with C-terminal polyhistidine tag

<400> SEQUENCE: 4

Gln Pro Phe Pro Cys Pro Pro Ala Cys Lys Cys Val Phe Arg Asp Ala
1               5                   10                  15
Ala Gln Cys Ser Gly Gly Asp Val Ala Arg Ile Ser Ala Leu Gly Leu
            20                  25                  30
Pro Thr Asn Leu Thr His Ile Leu Leu Phe Gly Met Gly Arg Gly Val
        35                  40                  45
Leu Gln Ser Gln Ser Phe Ser Gly Met Thr Val Leu Gln Arg Leu Met
    50                  55                  60
Ile Ser Asp Ser His Ile Ser Ala Val Ala Pro Gly Thr Phe Ser Asp
65                  70                  75                  80
Leu Ile Lys Leu Lys Thr Leu Arg Leu Ser Arg Asn Lys Ile Thr His
                85                  90                  95
Leu Pro Gly Ala Leu Leu Asp Lys Met Val Leu Leu Glu Gln Leu Phe
            100                 105                 110
Leu Asp His Asn Ala Leu Arg Gly Ile Asp Gln Asn Met Phe Gln Lys
        115                 120                 125
Leu Val Asn Leu Gln Glu Leu Ala Leu Asn Gln Asn Gln Leu Asp Phe
    130                 135                 140
Leu Pro Ala Ser Leu Phe Thr Asn Leu Glu Asn Leu Lys Leu Leu Asp
145                 150                 155                 160
Leu Ser Gly Asn Asn Leu Thr His Leu Pro Lys Gly Leu Leu Gly Ala
                165                 170                 175
Gln Ala Lys Leu Glu Arg Leu Leu His Ser Asn Arg Leu Val Ser
            180                 185                 190
Leu Asp Ser Gly Leu Leu Asn Ser Leu Gly Ala Leu Thr Glu Leu Gln
        195                 200                 205
Phe His Arg Asn His Ile Arg Ser Ile Ala Pro Gly Ala Phe Asp Arg
```

```
                    210                 215                 220
Leu Pro Asn Leu Ser Ser Leu Thr Leu Ser Arg Asn His Leu Ala Phe
225                 230                 235                 240

Leu Pro Ser Ala Leu Phe Leu His Ser His Asn Leu Thr Leu Leu Thr
                245                 250                 255

Leu Phe Glu Asn Pro Leu Ala Glu Leu Pro Gly Val Leu Phe Gly Glu
            260                 265                 270

Met Gly Gly Leu Gln Glu Leu Trp Leu Asn Arg Thr Gln Leu Arg Thr
        275                 280                 285

Leu Pro Ala Ala Ala Phe Arg Asn Leu Ser Arg Leu Arg Tyr Leu Gly
    290                 295                 300

Val Thr Leu Ser Pro Arg Leu Ser Ala Leu Pro Gln Gly Ala Phe Gln
305                 310                 315                 320

Gly Leu Gly Glu Leu Gln Val Leu Ala Leu His Ser Asn Gly Leu Thr
                325                 330                 335

Ala Leu Pro Asp Gly Leu Leu Arg Gly Leu Gly Lys Leu Arg Gln Val
            340                 345                 350

Ser Leu Arg Arg Asn Arg Leu Arg Ala Leu Pro Arg Ala Leu Phe Arg
        355                 360                 365

Asn Leu Ser Ser Leu Glu Ser Val Gln Leu Asp His Asn Gln Leu Glu
    370                 375                 380

Thr Leu Pro Gly Asp Val Phe Gly Ala Leu Pro Arg Leu Thr Glu Val
385                 390                 395                 400

Leu Leu Gly His Asn Ser Trp Arg Cys Asp Cys Gly Leu Gly Pro Phe
                405                 410                 415

Leu Gly Trp Leu Arg Gln His Leu Gly Leu Val Gly Gly Glu Glu Pro
            420                 425                 430

Pro Arg Cys Ala Gly Pro Gly Ala His Ala Gly Leu Pro Leu Trp Ala
        435                 440                 445

Leu Pro Gly Gly Asp Ala Glu Cys Pro Gly Pro Arg Gly Pro Pro Pro
    450                 455                 460

Arg Pro Ala Ala Asp Ser Ser Glu Ala Pro Val His Pro Ala Leu
465                 470                 475                 480

Ala Pro Asn Ser Ser Glu Pro Trp Val Trp Ala Gln Pro Val Thr Thr
                485                 490                 495

Gly Lys Gly Gln Asp His Ser Pro Phe Trp Gly Phe Tyr Phe Leu Leu
            500                 505                 510

Leu Ala Val Gln Ala His His His His His His His His
        515                 520                 525

<210> SEQ ID NO 5
<211> LENGTH: 2215
<212> TYPE: DNA
<213> ORGANISM: Mus musculus
<220> FEATURE:
<221> NAME/KEY: CDS
<222> LOCATION: (30)..(1733)

<400> SEQUENCE: 5
tcagtccagg gtgcagaact gcttcagac atg cta aga agc gcc ctg ctg tcc        53
                                Met Leu Arg Ser Ala Leu Leu Ser
                                  1               5 gcg gtg ctc gca ctc ttg cgt gcc caa cct ttt ccc tgc ccc aaa acc       101
Ala Val Leu Ala Leu Leu Arg Ala Gln Pro Phe Pro Cys Pro Lys Thr
         10                  15                  20 tgc aag tgt gtg gtc cgc gat gcc gcg cag tgc tcg ggc ggc agc gtg       149
```

```
         Cys Lys Cys Val Val Arg Asp Ala Ala Gln Cys Ser Gly Gly Ser Val
          25                  30                  35                  40 gct cac atc gct gag cta ggt ctg cct acg aac ctc aca cac atc ctg         197
Ala His Ile Ala Glu Leu Gly Leu Pro Thr Asn Leu Thr His Ile Leu
                         45                  50                  55 ctc ttc cga atg gac cag ggc ata ttg cgg aac cac agc ttc agc ggc         245
Leu Phe Arg Met Asp Gln Gly Ile Leu Arg Asn His Ser Phe Ser Gly
                 60                  65                  70 atg aca gtc ctt cag cgc ctg atg ctc tca gat agc cac att tcc gcc         293
Met Thr Val Leu Gln Arg Leu Met Leu Ser Asp Ser His Ile Ser Ala
             75                  80                  85 atc gac ccc ggc acc ttc aat gac ctg gta aaa ctg aaa acc ctc agg         341
Ile Asp Pro Gly Thr Phe Asn Asp Leu Val Lys Leu Lys Thr Leu Arg
         90                  95                 100 ttg acg cgc aac aaa atc tct cgt ctt cca cgt gcg atc ctg gat aag         389
Leu Thr Arg Asn Lys Ile Ser Arg Leu Pro Arg Ala Ile Leu Asp Lys
        105                 110                 115                 120 atg gta ctc ttg gaa cag ctg ttc ttg gac cac aat gca cta agg gac         437
Met Val Leu Leu Glu Gln Leu Phe Leu Asp His Asn Ala Leu Arg Asp
                         125                 130                 135 ctt gat caa aac ctg ttt cag caa ctg cgt aac ctt cag gag ctc ggt         485
Leu Asp Gln Asn Leu Phe Gln Gln Leu Arg Asn Leu Gln Glu Leu Gly
                 140                 145                 150 ttg aac cag aat cag ctc tct ttt ctt cct gct aac ctt ttc tcg agc         533
Leu Asn Gln Asn Gln Leu Ser Phe Leu Pro Ala Asn Leu Phe Ser Ser
            155                 160                 165 ctg aga gaa ctg aag ttg ttg gat tta tcg cga aac aac ctg acc cac         581
Leu Arg Glu Leu Lys Leu Leu Asp Leu Ser Arg Asn Asn Leu Thr His
        170                 175                 180 ctg ccc aag gga ctg ctt ggg gct caa gtt aag ctt gag aaa ctg ctg         629
Leu Pro Lys Gly Leu Leu Gly Ala Gln Val Lys Leu Glu Lys Leu Leu
185                 190                 195                 200 ctc tat tca aac cag ctc acg tct gtg gat tcg ggg ctg ctg agc aac         677
Leu Tyr Ser Asn Gln Leu Thr Ser Val Asp Ser Gly Leu Leu Ser Asn
                         205                 210                 215 ctg ggc gcc ctg act gag ctg cgg ctg gag cgg aat cac ctc cgc tcc         725
Leu Gly Ala Leu Thr Glu Leu Arg Leu Glu Arg Asn His Leu Arg Ser
                 220                 225                 230 gta gcc ccg ggt gcc ttc gac cgc ctc gga aac ctg agc tcc ttg act         773
Val Ala Pro Gly Ala Phe Asp Arg Leu Gly Asn Leu Ser Ser Leu Thr
            235                 240                 245 cta tcc gga aac ctc ctg gag tct ctg ccg ccc gcg ctc ttc ctt cac         821
Leu Ser Gly Asn Leu Leu Glu Ser Leu Pro Pro Ala Leu Phe Leu His
        250                 255                 260 gtg agc agc gtg tct cgg ctg act ctg ttc gag aac ccc ctg gag gag         869
Val Ser Ser Val Ser Arg Leu Thr Leu Phe Glu Asn Pro Leu Glu Glu
265                 270                 275                 280 ctc ccg gac gtg ttg ttc ggg gag atg gcc ggc ctg cgg gag ctg tgg         917
Leu Pro Asp Val Leu Phe Gly Glu Met Ala Gly Leu Arg Glu Leu Trp
                         285                 290                 295 ctg aac ggc acc cac ctg agc acg ctg ccc gcc gct gcc ttc cgc aac         965
Leu Asn Gly Thr His Leu Ser Thr Leu Pro Ala Ala Ala Phe Arg Asn
                 300                 305                 310 ctg agc ggc ttg cag acg ctg ggg ctg acg cgg aac ccg cgc ctg agc        1013
Leu Ser Gly Leu Gln Thr Leu Gly Leu Thr Arg Asn Pro Arg Leu Ser
            315                 320                 325 gcg ctc ccg cgc ggc gtg ttc cag ggc cta cgg gag ctg cgc gtg ctc        1061
Ala Leu Pro Arg Gly Val Phe Gln Gly Leu Arg Glu Leu Arg Val Leu
        330                 335                 340
```

```
gcg ctg cac acc aac gcc ctg gcg gag ctg cgg gac gac gcg ctg cgc       1109
Ala Leu His Thr Asn Ala Leu Ala Glu Leu Arg Asp Asp Ala Leu Arg
345             350                 355                 360 ggc ctc ggg cac ctg cgc cag gtg tcg ctg cgc cac aac cgg ctg cgg       1157
Gly Leu Gly His Leu Arg Gln Val Ser Leu Arg His Asn Arg Leu Arg
            365                 370                 375 gcc ctg ccc cgc acg ctc ttc cgc aac ctc agc agc ctc gag agc gtg       1205
Ala Leu Pro Arg Thr Leu Phe Arg Asn Leu Ser Ser Leu Glu Ser Val
        380                 385                 390 cag cta gag cac aac cag ctg gag acg ctg cca gga gac gtg ttc gcg       1253
Gln Leu Glu His Asn Gln Leu Glu Thr Leu Pro Gly Asp Val Phe Ala
    395                 400                 405 gct ctg ccc cag ctg acc cag gtc ctg ctg ggt cac aac ccc tgg ctc       1301
Ala Leu Pro Gln Leu Thr Gln Val Leu Leu Gly His Asn Pro Trp Leu
410                 415                 420 tgc gac tgt ggc ctg tgg ccc ttc ctc cag tgg ctg cgg cat cac ccg       1349
Cys Asp Cys Gly Leu Trp Pro Phe Leu Gln Trp Leu Arg His His Pro
425             430                 435                 440 gac atc ctg ggc cga gac gag ccc ccg cag tgc cgt ggc ccg gag cca       1397
Asp Ile Leu Gly Arg Asp Glu Pro Pro Gln Cys Arg Gly Pro Glu Pro
            445                 450                 455 cgc gcc agc ctg tcg ttc tgg gag ctg ctg cag ggt gac ccg tgg tgc       1445
Arg Ala Ser Leu Ser Phe Trp Glu Leu Leu Gln Gly Asp Pro Trp Cys
        460                 465                 470 ccg gat cct cgc agc ctg cct ctc gac cct cca acc gaa aat gct ctg       1493
Pro Asp Pro Arg Ser Leu Pro Leu Asp Pro Pro Thr Glu Asn Ala Leu
    475                 480                 485 gaa gcc ccg gtt ccg tcc tgg ctg cct aac agc tgg cag tcc cag acg       1541
Glu Ala Pro Val Pro Ser Trp Leu Pro Asn Ser Trp Gln Ser Gln Thr
490                 495                 500 tgg gcc cag ctg gtg gcc agg ggt gaa agt ccc aat aac agg ctc tac       1589
Trp Ala Gln Leu Val Ala Arg Gly Glu Ser Pro Asn Asn Arg Leu Tyr
505             510                 515                 520 tgg ggt ctt tat att ctg ctt cta gta gcc cag gcc atc ata gcc gcg       1637
Trp Gly Leu Tyr Ile Leu Leu Leu Val Ala Gln Ala Ile Ile Ala Ala
            525                 530                 535 ttc atc gtg ttt gcc atg att aaa atc ggc cag ctg ttt cga aca tta       1685
Phe Ile Val Phe Ala Met Ile Lys Ile Gly Gln Leu Phe Arg Thr Leu
        540                 545                 550 atc aga gag aag ctc ttg tta gag gca atg gga aaa tcg tgt aac taa       1733
Ile Arg Glu Lys Leu Leu Leu Glu Ala Met Gly Lys Ser Cys Asn
    555                 560                 565 tgaaactgac cagagcattg tggacggggc cccaaggaga atgcagtcag gatgctggcg    1793
tgccattaca ctatttccca ggccttttct cctctcccgt gctcttagtg tctcttcttc    1853 tccctctct tcagaagtag cttttgtaaa tcgctactgc tttctagcct ggcctgggtt     1913
acctcctctg ctgttagttt caaggggggct gagggtgggg gttcgacggg acttggctca   1973
tcaggtccaa ctgtgcagcg ctgggtgcct agtggagaga ggagcccttt cttggtttct    2033
gaatttgagg acacatcctg ccagtgggca agacctctcc gggacccagc aagggttgag    2093
taacatttgc tgaaggaaca ccggcttaaa acgaacccta ggtccaagag atgaaggctc    2153
ttcccaaaat aaaggtggag tgttcttgtc cctttacctg aaaggaaaaa aaaaaaaaa     2213 aa                                                                  2215
```

<210> SEQ ID NO 6
<211> LENGTH: 567
<212> TYPE: PRT
<213> ORGANISM: Mus musculus

<400> SEQUENCE: 6

```
Met Leu Arg Ser Ala Leu Leu Ser Ala Val Leu Ala Leu Leu Arg Ala
1               5                   10                  15

Gln Pro Phe Pro Cys Pro Lys Thr Cys Lys Cys Val Val Arg Asp Ala
            20                  25                  30

Ala Gln Cys Ser Gly Gly Ser Val Ala His Ile Ala Glu Leu Gly Leu
        35                  40                  45

Pro Thr Asn Leu Thr His Ile Leu Leu Phe Arg Met Asp Gln Gly Ile
    50                  55                  60

Leu Arg Asn His Ser Phe Ser Gly Met Thr Val Leu Gln Arg Leu Met
65                  70                  75                  80

Leu Ser Asp Ser His Ile Ser Ala Ile Asp Pro Gly Thr Phe Asn Asp
                85                  90                  95

Leu Val Lys Leu Lys Thr Leu Arg Leu Thr Arg Asn Lys Ile Ser Arg
            100                 105                 110

Leu Pro Arg Ala Ile Leu Asp Lys Met Val Leu Leu Glu Gln Leu Phe
        115                 120                 125

Leu Asp His Asn Ala Leu Arg Asp Leu Asp Gln Asn Leu Phe Gln Gln
    130                 135                 140

Leu Arg Asn Leu Gln Glu Leu Gly Leu Asn Gln Asn Gln Leu Ser Phe
145                 150                 155                 160

Leu Pro Ala Asn Leu Phe Ser Ser Leu Arg Glu Leu Lys Leu Leu Asp
                165                 170                 175

Leu Ser Arg Asn Asn Leu Thr His Leu Pro Lys Gly Leu Leu Gly Ala
            180                 185                 190

Gln Val Lys Leu Glu Lys Leu Leu Leu Tyr Ser Asn Gln Leu Thr Ser
        195                 200                 205

Val Asp Ser Gly Leu Leu Ser Asn Leu Gly Ala Leu Thr Glu Leu Arg
    210                 215                 220

Leu Glu Arg Asn His Leu Arg Ser Val Ala Pro Gly Ala Phe Asp Arg
225                 230                 235                 240

Leu Gly Asn Leu Ser Ser Leu Thr Leu Ser Gly Asn Leu Leu Glu Ser
                245                 250                 255

Leu Pro Pro Ala Leu Phe Leu His Val Ser Ser Val Ser Arg Leu Thr
            260                 265                 270

Leu Phe Glu Asn Pro Leu Glu Glu Leu Pro Asp Val Leu Phe Gly Glu
        275                 280                 285

Met Ala Gly Leu Arg Glu Leu Trp Leu Asn Gly Thr His Leu Ser Thr
    290                 295                 300

Leu Pro Ala Ala Ala Phe Arg Asn Leu Ser Gly Leu Gln Thr Leu Gly
305                 310                 315                 320

Leu Thr Arg Asn Pro Arg Leu Ser Ala Leu Pro Arg Gly Val Phe Gln
                325                 330                 335

Gly Leu Arg Glu Leu Arg Val Leu Ala Leu His Thr Asn Ala Leu Ala
            340                 345                 350

Glu Leu Arg Asp Asp Ala Leu Arg Gly Leu Gly His Leu Arg Gln Val
        355                 360                 365

Ser Leu Arg His Asn Arg Leu Arg Ala Leu Pro Arg Thr Leu Phe Arg
    370                 375                 380

Asn Leu Ser Ser Leu Glu Ser Val Gln Leu Glu His Asn Gln Leu Glu
385                 390                 395                 400

Thr Leu Pro Gly Asp Val Phe Ala Ala Leu Pro Gln Leu Thr Gln Val
```

```
                405                 410                 415
Leu Leu Gly His Asn Pro Trp Leu Cys Asp Cys Gly Leu Trp Pro Phe
            420                 425                 430

Leu Gln Trp Leu Arg His His Pro Asp Ile Leu Gly Arg Asp Glu Pro
            435                 440                 445

Pro Gln Cys Arg Gly Pro Glu Pro Arg Ala Ser Leu Ser Phe Trp Glu
            450                 455                 460

Leu Leu Gln Gly Asp Pro Trp Cys Pro Asp Pro Arg Ser Leu Pro Leu
465                 470                 475                 480

Asp Pro Pro Thr Glu Asn Ala Leu Glu Ala Pro Val Pro Ser Trp Leu
            485                 490                 495

Pro Asn Ser Trp Gln Ser Gln Thr Trp Ala Gln Leu Val Ala Arg Gly
            500                 505                 510

Glu Ser Pro Asn Asn Arg Leu Tyr Trp Gly Leu Tyr Ile Leu Leu Leu
            515                 520                 525

Val Ala Gln Ala Ile Ile Ala Ala Phe Ile Val Phe Ala Met Ile Lys
            530                 535                 540

Ile Gly Gln Leu Phe Arg Thr Leu Ile Arg Glu Lys Leu Leu Leu Glu
545                 550                 555                 560

Ala Met Gly Lys Ser Cys Asn
            565

<210> SEQ ID NO 7
<211> LENGTH: 551
<212> TYPE: PRT
<213> ORGANISM: Mus musculus

<400> SEQUENCE: 7

Gln Pro Phe Pro Cys Pro Lys Thr Cys Lys Cys Val Val Arg Asp Ala
1               5                   10                  15

Ala Gln Cys Ser Gly Gly Ser Val Ala His Ile Ala Glu Leu Gly Leu
            20                  25                  30

Pro Thr Asn Leu Thr His Ile Leu Leu Phe Arg Met Asp Gln Gly Ile
            35                  40                  45

Leu Arg Asn His Ser Phe Ser Gly Met Thr Val Leu Gln Arg Leu Met
        50                  55                  60

Leu Ser Asp Ser His Ile Ser Ala Ile Asp Pro Gly Thr Phe Asn Asp
65                  70                  75                  80

Leu Val Lys Leu Lys Thr Leu Arg Leu Thr Arg Asn Lys Ile Ser Arg
            85                  90                  95

Leu Pro Arg Ala Ile Leu Asp Lys Met Val Leu Leu Glu Gln Leu Phe
            100                 105                 110

Leu Asp His Asn Ala Leu Arg Asp Leu Asp Gln Asn Leu Phe Gln Gln
            115                 120                 125

Leu Arg Asn Leu Gln Glu Leu Gly Leu Asn Gln Asn Gln Leu Ser Phe
        130                 135                 140

Leu Pro Ala Asn Leu Phe Ser Ser Leu Arg Glu Leu Lys Leu Leu Asp
145                 150                 155                 160

Leu Ser Arg Asn Asn Leu Thr His Leu Pro Lys Gly Leu Leu Gly Ala
            165                 170                 175

Gln Val Lys Leu Glu Lys Leu Leu Leu Tyr Ser Asn Gln Leu Thr Ser
            180                 185                 190

Val Asp Ser Gly Leu Leu Ser Asn Leu Gly Ala Leu Thr Glu Leu Arg
            195                 200                 205
```

```
Leu Glu Arg Asn His Leu Arg Ser Val Ala Pro Gly Ala Phe Asp Arg
        210                 215                 220

Leu Gly Asn Leu Ser Ser Leu Thr Leu Ser Gly Asn Leu Leu Glu Ser
225                 230                 235                 240

Leu Pro Pro Ala Leu Phe Leu His Val Ser Ser Val Ser Arg Leu Thr
                245                 250                 255

Leu Phe Glu Asn Pro Leu Glu Glu Leu Pro Asp Val Leu Phe Gly Glu
            260                 265                 270

Met Ala Gly Leu Arg Glu Leu Trp Leu Asn Gly Thr His Leu Ser Thr
        275                 280                 285

Leu Pro Ala Ala Ala Phe Arg Asn Leu Ser Gly Leu Gln Thr Leu Gly
        290                 295                 300

Leu Thr Arg Asn Pro Arg Leu Ser Ala Leu Pro Arg Gly Val Phe Gln
305                 310                 315                 320

Gly Leu Arg Glu Leu Arg Val Leu Ala Leu His Thr Asn Ala Leu Ala
                325                 330                 335

Glu Leu Arg Asp Asp Ala Leu Arg Gly Leu Gly His Leu Arg Gln Val
            340                 345                 350

Ser Leu Arg His Asn Arg Leu Arg Ala Leu Pro Arg Thr Leu Phe Arg
        355                 360                 365

Asn Leu Ser Ser Leu Glu Ser Val Gln Leu Glu His Asn Gln Leu Glu
        370                 375                 380

Thr Leu Pro Gly Asp Val Phe Ala Ala Leu Pro Gln Leu Thr Gln Val
385                 390                 395                 400

Leu Leu Gly His Asn Pro Trp Leu Cys Asp Cys Gly Leu Trp Pro Phe
                405                 410                 415

Leu Gln Trp Leu Arg His His Pro Asp Ile Leu Gly Arg Asp Glu Pro
            420                 425                 430

Pro Gln Cys Arg Gly Pro Glu Pro Arg Ala Ser Leu Ser Phe Trp Glu
        435                 440                 445

Leu Leu Gln Gly Asp Pro Trp Cys Pro Asp Pro Arg Ser Leu Pro Leu
        450                 455                 460

Asp Pro Pro Thr Glu Asn Ala Leu Glu Ala Pro Val Pro Ser Trp Leu
465                 470                 475                 480

Pro Asn Ser Trp Gln Ser Gln Thr Trp Ala Gln Leu Val Ala Arg Gly
                485                 490                 495

Glu Ser Pro Asn Asn Arg Leu Tyr Trp Gly Leu Tyr Ile Leu Leu Leu
            500                 505                 510

Val Ala Gln Ala Ile Ile Ala Ala Phe Ile Val Phe Ala Met Ile Lys
        515                 520                 525

Ile Gly Gln Leu Phe Arg Thr Leu Ile Arg Glu Lys Leu Leu Leu Glu
        530                 535                 540

Ala Met Gly Lys Ser Cys Asn
545                 550

<210> SEQ ID NO 8
<211> LENGTH: 527
<212> TYPE: PRT
<213> ORGANISM: Artificial Sequence
<220> FEATURE:
<223> OTHER INFORMATION: Soluble murine Glycoprotein V with C-terminal
      FLAG tag

<400> SEQUENCE: 8

Gln Pro Phe Pro Cys Pro Lys Thr Cys Lys Cys Val Val Arg Asp Ala
1               5                   10                  15
```

```
Ala Gln Cys Ser Gly Gly Ser Val Ala His Ile Ala Glu Leu Gly Leu
                20                  25                  30

Pro Thr Asn Leu Thr His Ile Leu Leu Phe Arg Met Asp Gln Gly Ile
            35                  40                  45

Leu Arg Asn His Ser Phe Ser Gly Met Thr Val Leu Gln Arg Gln Met
 50                  55                  60

Leu Ser Asp Ser His Ile Ser Ala Ile Asp Pro Gly Thr Phe Asn Asp
 65                  70                  75                  80

Leu Val Lys Leu Lys Thr Leu Arg Leu Thr Arg Asn Lys Ile Ser Arg
                85                  90                  95

Leu Pro Arg Ala Ile Leu Asp Lys Met Val Leu Leu Glu Gln Leu Phe
            100                 105                 110

Leu Asp His Asn Ala Leu Arg Asp Leu Asp Gln Asn Leu Phe Gln Gln
        115                 120                 125

Leu Arg Asn Leu Gln Glu Leu Gly Leu Asn Asn Gln Leu Ser Phe
130                 135                 140

Leu Pro Ala Asn Leu Phe Ser Ser Leu Arg Glu Leu Lys Leu Leu Asp
145                 150                 155                 160

Leu Ser Arg Asn Asn Leu Thr His Leu Pro Lys Gly Leu Leu Gly Ala
                165                 170                 175

Gln Val Lys Leu Glu Lys Leu Leu Leu Tyr Ser Asn Gln Leu Thr Ser
            180                 185                 190

Val Asp Ser Gly Leu Leu Ser Asn Leu Gly Ala Leu Thr Glu Leu Arg
        195                 200                 205

Leu Glu Arg Asn His Leu Arg Ser Val Ala Pro Gly Ala Phe Asp Arg
    210                 215                 220

Leu Gly Asn Leu Ser Ser Leu Thr Leu Ser Gly Asn Leu Leu Glu Ser
225                 230                 235                 240

Leu Pro Pro Ala Leu Phe Leu His Val Ser Ser Val Ser Arg Leu Thr
                245                 250                 255

Leu Phe Glu Asn Pro Leu Glu Glu Leu Pro Asp Val Leu Phe Gly Glu
            260                 265                 270

Met Ala Gly Leu Arg Glu Leu Trp Leu Asn Gly Thr His Leu Ser Thr
        275                 280                 285

Leu Pro Ala Ala Ala Phe Arg Asn Leu Ser Gly Leu Gln Thr Leu Gly
    290                 295                 300

Leu Thr Arg Asn Pro Arg Leu Ser Ala Leu Pro Arg Gly Val Phe Gln
305                 310                 315                 320

Gly Leu Arg Glu Leu Arg Val Leu Gly Leu His Thr Asn Ala Leu Ala
                325                 330                 335

Glu Leu Arg Asp Asp Ala Leu Arg Gly Leu Gly His Leu Arg Gln Val
            340                 345                 350

Ser Leu Arg His Asn Arg Leu Arg Ala Leu Pro Arg Thr Leu Phe Arg
        355                 360                 365

Asn Leu Ser Ser Leu Glu Ser Val Gln Leu Glu His Asn Gln Leu Glu
    370                 375                 380

Thr Leu Pro Gly Asp Val Phe Ala Ala Leu Pro Gln Leu Thr Gln Val
385                 390                 395                 400

Leu Leu Gly His Asn Pro Trp Leu Cys Asp Cys Gly Leu Trp Arg Phe
                405                 410                 415

Leu Gln Trp Leu Arg His His Pro Asp Ile Leu Gly Arg Asp Glu Pro
            420                 425                 430
```

```
Pro Gln Cys Arg Gly Pro Glu Pro Arg Ala Ser Leu Ser Phe Trp Glu
            435                 440                 445

Leu Leu Gln Gly Asp Pro Trp Cys Pro Asp Pro Arg Ser Leu Pro Leu
    450                 455                 460

Asp Pro Pro Thr Glu Asn Ala Leu Glu Ala Pro Val Pro Ser Trp Leu
465                 470                 475                 480

Pro Asn Ser Trp Gln Ser Gln Thr Trp Ala Gln Leu Val Ala Arg Gly
                485                 490                 495

Glu Ser Pro Asn Asn Arg Leu Glu Cys Gly Arg Asn Pro Ala Phe Leu
                500                 505                 510

Tyr Lys Val Val Leu Glu Met Asp Tyr Lys Asp Asp Asp Lys
            515                 520                 525

<210> SEQ ID NO 9
<211> LENGTH: 1078
<212> TYPE: PRT
<213> ORGANISM: Artificial Sequence
<220> FEATURE:
<223> OTHER INFORMATION: Soluble human GPV fused to albumin via linker
      (without signal peptide)
<220> FEATURE:
<221> NAME/KEY: MISC_FEATURE
<222> LOCATION: (1)..(457)
<223> OTHER INFORMATION: human GPV
<220> FEATURE:
<221> NAME/KEY: MISC_FEATURE
<222> LOCATION: (458)..(463)
<223> OTHER INFORMATION: thrombin cleavage site
<220> FEATURE:
<221> NAME/KEY: MISC_FEATURE
<222> LOCATION: (464)..(493)
<223> OTHER INFORMATION: GGS linker
<220> FEATURE:
<221> NAME/KEY: MISC_FEATURE
<222> LOCATION: (494)..(1078)
<223> OTHER INFORMATION: human albumin

<400> SEQUENCE: 9

Gln Pro Phe Pro Cys Pro Pro Ala Cys Lys Cys Val Phe Arg Asp Ala
1               5                   10                  15

Ala Gln Cys Ser Gly Gly Asp Val Ala Arg Ile Ser Ala Leu Gly Leu
            20                  25                  30

Pro Thr Asn Leu Thr His Ile Leu Leu Phe Gly Met Gly Arg Gly Val
        35                  40                  45

Leu Gln Ser Gln Ser Phe Ser Gly Met Thr Val Leu Gln Arg Leu Met
    50                  55                  60

Ile Ser Asp Ser His Ile Ser Ala Val Ala Pro Gly Thr Phe Ser Asp
65                  70                  75                  80

Leu Ile Lys Leu Lys Thr Leu Arg Leu Ser Arg Asn Lys Ile Thr His
                85                  90                  95

Leu Pro Gly Ala Leu Leu Asp Lys Met Val Leu Leu Glu Gln Leu Phe
            100                 105                 110

Leu Asp His Asn Ala Leu Arg Gly Ile Asp Gln Asn Met Phe Gln Lys
        115                 120                 125

Leu Val Asn Leu Gln Glu Leu Ala Leu Asn Gln Asn Gln Leu Asp Phe
    130                 135                 140

Leu Pro Ala Ser Leu Phe Thr Asn Leu Glu Asn Leu Lys Leu Leu Asp
145                 150                 155                 160

Leu Ser Gly Asn Asn Leu Thr His Leu Pro Lys Gly Leu Leu Gly Ala
                165                 170                 175

Gln Ala Lys Leu Glu Arg Leu Leu Leu His Ser Asn Arg Leu Val Ser
```

```
                180              185                190
Leu Asp Ser Gly Leu Leu Asn Ser Leu Gly Ala Leu Thr Glu Leu Gln
                195                  200                  205

Phe His Arg Asn His Ile Arg Ser Ile Ala Pro Gly Ala Phe Asp Arg
            210                  215                  220

Leu Pro Asn Leu Ser Ser Leu Thr Leu Ser Arg Asn His Leu Ala Phe
225                  230                  235                  240

Leu Pro Ser Ala Leu Phe Leu His Ser His Asn Leu Thr Leu Leu Thr
                245                  250                  255

Leu Phe Glu Asn Pro Leu Ala Glu Leu Pro Gly Val Leu Phe Gly Glu
            260                  265                  270

Met Gly Gly Leu Gln Glu Leu Trp Leu Asn Arg Thr Gln Leu Arg Thr
                275                  280                  285

Leu Pro Ala Ala Ala Phe Arg Asn Leu Ser Arg Leu Arg Tyr Leu Gly
            290                  295                  300

Val Thr Leu Ser Pro Arg Leu Ser Ala Leu Pro Gln Gly Ala Phe Gln
305                  310                  315                  320

Gly Leu Gly Glu Leu Gln Val Leu Ala Leu His Ser Asn Gly Leu Thr
                325                  330                  335

Ala Leu Pro Asp Gly Leu Leu Arg Gly Leu Gly Lys Leu Arg Gln Val
            340                  345                  350

Ser Leu Arg Arg Asn Arg Leu Arg Ala Leu Pro Arg Ala Leu Phe Arg
355                  360                  365

Asn Leu Ser Ser Leu Glu Ser Val Gln Leu Asp His Asn Gln Leu Glu
            370                  375                  380

Thr Leu Pro Gly Asp Val Phe Gly Ala Leu Pro Arg Leu Thr Glu Val
385                  390                  395                  400

Leu Leu Gly His Asn Ser Trp Arg Cys Asp Cys Gly Leu Gly Pro Phe
                405                  410                  415

Leu Gly Trp Leu Arg Gln His Leu Gly Leu Val Gly Gly Glu Glu Pro
            420                  425                  430

Pro Arg Cys Ala Gly Pro Gly Ala His Ala Gly Leu Pro Leu Trp Ala
            435                  440                  445

Leu Pro Gly Gly Asp Ala Glu Cys Pro Gly Pro Arg Ala Val Gly Ser
450                  455                  460

Gly Gly Ser Gly Gly Ser Gly Gly Ser Gly Gly Ser Gly Gly Ser Gly
465                  470                  475                  480

Gly Ser Gly Gly Ser Gly Gly Ser Gly Gly Ser Asp Ala His
            485                  490                  495

Lys Ser Glu Val Ala His Arg Phe Lys Asp Leu Gly Glu Glu Asn Phe
            500                  505                  510

Lys Ala Leu Val Leu Ile Ala Phe Ala Gln Tyr Leu Gln Gln Cys Pro
            515                  520                  525

Phe Glu Asp His Val Lys Leu Val Asn Glu Val Thr Glu Phe Ala Lys
            530                  535                  540

Thr Cys Val Ala Asp Glu Ser Ala Glu Asn Cys Asp Lys Ser Leu His
545                  550                  555                  560

Thr Leu Phe Gly Asp Lys Leu Cys Thr Val Ala Thr Leu Arg Glu Thr
                565                  570                  575

Tyr Gly Glu Met Ala Asp Cys Cys Ala Lys Gln Glu Pro Glu Arg Asn
            580                  585                  590

Glu Cys Phe Leu Gln His Lys Asp Asp Asn Pro Asn Leu Pro Arg Leu
            595                  600                  605
```

```
Val Arg Pro Glu Val Asp Val Met Cys Thr Ala Phe His Asp Asn Glu
610                 615                 620

Glu Thr Phe Leu Lys Lys Tyr Leu Tyr Glu Ile Ala Arg Arg His Pro
625                 630                 635                 640

Tyr Phe Tyr Ala Pro Glu Leu Leu Phe Phe Ala Lys Arg Tyr Lys Ala
                645                 650                 655

Ala Phe Thr Glu Cys Cys Gln Ala Ala Asp Lys Ala Ala Cys Leu Leu
                660                 665                 670

Pro Lys Leu Asp Glu Leu Arg Asp Glu Gly Lys Ala Ser Ser Ala Lys
                675                 680                 685

Gln Arg Leu Lys Cys Ala Ser Leu Gln Lys Phe Gly Glu Arg Ala Phe
690                 695                 700

Lys Ala Trp Ala Val Ala Arg Leu Ser Gln Arg Phe Pro Lys Ala Glu
705                 710                 715                 720

Phe Ala Glu Val Ser Lys Leu Val Thr Asp Leu Thr Lys Val His Thr
                725                 730                 735

Glu Cys Cys His Gly Asp Leu Leu Glu Cys Ala Asp Asp Arg Ala Asp
                740                 745                 750

Leu Ala Lys Tyr Ile Cys Glu Asn Gln Asp Ser Ile Ser Ser Lys Leu
                755                 760                 765

Lys Glu Cys Cys Glu Lys Pro Leu Leu Glu Lys Ser His Cys Ile Ala
770                 775                 780

Glu Val Glu Asn Asp Glu Met Pro Ala Asp Leu Pro Ser Leu Ala Ala
785                 790                 795                 800

Asp Phe Val Glu Ser Lys Asp Val Cys Lys Asn Tyr Ala Glu Ala Lys
                805                 810                 815

Asp Val Phe Leu Gly Met Phe Leu Tyr Glu Tyr Ala Arg Arg His Pro
                820                 825                 830

Asp Tyr Ser Val Val Leu Leu Arg Leu Ala Lys Thr Tyr Glu Thr
                835                 840                 845

Thr Leu Glu Lys Cys Cys Ala Ala Ala Asp Pro His Glu Cys Tyr Ala
850                 855                 860

Lys Val Phe Asp Glu Phe Lys Pro Leu Val Glu Glu Pro Gln Asn Leu
865                 870                 875                 880

Ile Lys Gln Asn Cys Glu Leu Phe Glu Gln Leu Gly Glu Tyr Lys Phe
                885                 890                 895

Gln Asn Ala Leu Leu Val Arg Tyr Thr Lys Lys Val Pro Gln Val Ser
                900                 905                 910

Thr Pro Thr Leu Val Glu Val Ser Arg Asn Leu Gly Lys Val Gly Ser
                915                 920                 925

Lys Cys Cys Lys His Pro Glu Ala Lys Arg Met Pro Cys Ala Glu Asp
930                 935                 940

Tyr Leu Ser Val Val Leu Asn Gln Leu Cys Val Leu His Glu Lys Thr
945                 950                 955                 960

Pro Val Ser Asp Arg Val Thr Lys Cys Cys Thr Glu Ser Leu Val Asn
                965                 970                 975

Arg Arg Pro Cys Phe Ser Ala Leu Glu Val Asp Glu Thr Tyr Val Pro
                980                 985                 990

Lys Glu Phe Asn Ala Glu Thr Phe Thr Phe His Ala Asp Ile Cys Thr
                995                 1000                1005

Leu Ser Glu Lys Glu Arg Gln Ile Lys Lys Gln Thr Ala Leu Val
       1010                1015                1020
```

Glu Leu Val Lys His Lys Pro Lys Ala Thr Lys Glu Gln Leu Lys
    1025                1030                1035

Ala Val Met Asp Asp Phe Ala Ala Phe Val Glu Lys Cys Cys Lys
    1040                1045                1050

Ala Asp Asp Lys Glu Thr Cys Phe Ala Glu Glu Gly Lys Lys Leu
    1055                1060                1065

Val Ala Ala Ser Gln Ala Ala Leu Gly Leu
    1070                1075

<210> SEQ ID NO 10
<211> LENGTH: 460
<212> TYPE: PRT
<213> ORGANISM: Homo sapiens
<220> FEATURE:
<221> NAME/KEY: MISC_FEATURE
<222> LOCATION: (1)..(460)
<223> OTHER INFORMATION: fragment of human GPV obtained from thrombin
      cleavage (GPVf1)

<400> SEQUENCE: 10

Gln Pro Phe Pro Cys Pro Pro Ala Cys Lys Cys Val Phe Arg Asp Ala
1               5                   10                  15

Ala Gln Cys Ser Gly Gly Asp Val Ala Arg Ile Ser Ala Leu Gly Leu
            20                  25                  30

Pro Thr Asn Leu Thr His Ile Leu Leu Phe Gly Met Gly Arg Gly Val
            35                  40                  45

Leu Gln Ser Gln Ser Phe Ser Gly Met Thr Val Leu Gln Arg Leu Met
50                  55                  60

Ile Ser Asp Ser His Ile Ser Ala Val Ala Pro Gly Thr Phe Ser Asp
65                  70                  75                  80

Leu Ile Lys Leu Lys Thr Leu Arg Leu Ser Arg Asn Lys Ile Thr His
                85                  90                  95

Leu Pro Gly Ala Leu Leu Asp Lys Met Val Leu Leu Glu Gln Leu Phe
            100                 105                 110

Leu Asp His Asn Ala Leu Arg Gly Ile Asp Gln Asn Met Phe Gln Lys
            115                 120                 125

Leu Val Asn Leu Gln Glu Leu Ala Leu Asn Gln Asn Gln Leu Asp Phe
130                 135                 140

Leu Pro Ala Ser Leu Phe Thr Asn Leu Glu Asn Leu Lys Leu Leu Asp
145                 150                 155                 160

Leu Ser Gly Asn Asn Leu Thr His Leu Pro Lys Gly Leu Leu Gly Ala
                165                 170                 175

Gln Ala Lys Leu Glu Arg Leu Leu His Ser Asn Arg Leu Val Ser
            180                 185                 190

Leu Asp Ser Gly Leu Leu Asn Ser Leu Gly Ala Leu Thr Glu Leu Gln
            195                 200                 205

Phe His Arg Asn His Ile Arg Ser Ile Ala Pro Gly Ala Phe Asp Arg
210                 215                 220

Leu Pro Asn Leu Ser Ser Leu Thr Leu Ser Arg Asn His Leu Ala Phe
225                 230                 235                 240

Leu Pro Ser Ala Leu Phe Leu His Ser His Asn Leu Thr Leu Leu Thr
                245                 250                 255

Leu Phe Glu Asn Pro Leu Ala Glu Leu Pro Gly Val Leu Phe Gly Glu
            260                 265                 270

Met Gly Gly Leu Gln Glu Leu Trp Leu Asn Arg Thr Gln Leu Arg Thr
            275                 280                 285

-continued

```
Leu Pro Ala Ala Ala Phe Arg Asn Leu Ser Arg Leu Arg Tyr Leu Gly
    290                 295                 300

Val Thr Leu Ser Pro Arg Leu Ser Ala Leu Pro Gln Gly Ala Phe Gln
305                 310                 315                 320

Gly Leu Gly Glu Leu Gln Val Leu Ala Leu His Ser Asn Gly Leu Thr
                325                 330                 335

Ala Leu Pro Asp Gly Leu Leu Arg Gly Leu Gly Lys Leu Arg Gln Val
            340                 345                 350

Ser Leu Arg Arg Asn Arg Leu Arg Ala Leu Pro Arg Ala Leu Phe Arg
        355                 360                 365

Asn Leu Ser Ser Leu Glu Ser Val Gln Leu Asp His Asn Gln Leu Glu
    370                 375                 380

Thr Leu Pro Gly Asp Val Phe Gly Ala Leu Pro Arg Leu Thr Glu Val
385                 390                 395                 400

Leu Leu Gly His Asn Ser Trp Arg Cys Asp Cys Gly Leu Gly Pro Phe
                405                 410                 415

Leu Gly Trp Leu Arg Gln His Leu Gly Leu Val Gly Gly Glu Glu Pro
            420                 425                 430

Pro Arg Cys Ala Gly Pro Gly Ala His Ala Gly Leu Pro Leu Trp Ala
        435                 440                 445

Leu Pro Gly Gly Asp Ala Glu Cys Pro Gly Pro Arg
450                 455                 460
```

UNITED STATES PATENT AND TRADEMARK OFFICE
CERTIFICATE OF CORRECTION

PATENT NO. : 11,028,144 B2
APPLICATION NO. : 16/065365
DATED : June 8, 2021
INVENTOR(S) : Nieswandt et al.

Page 1 of 1

It is certified that error appears in the above-identified patent and that said Letters Patent is hereby corrected as shown below:

On the Title Page

Item (30), under "Foreign Application Priority Data,"
"Dec. 23, 2015 (EP) ............ 15202530" should read:
--Dec. 23, 2015 (EP) ............ 15202530.0--.

In the Claims

Claim 1, Column 59, Line 32, "A method for the treatment and/or prevention of" should read:
--A method for the treatment of--.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*